(12) United States Patent
Shu

(10) Patent No.: US 8,647,670 B2
(45) Date of Patent: Feb. 11, 2014

(54) BIOCOMPATIBLE RAPID-GELATING HYDROGEL AND ASSOCIATED PREPARATION METHOD OF SPRAY

(75) Inventor: Xiaozheng Shu, Shanghai (CN)

(73) Assignee: Bioregen Biomedical (Changzhou) Co., Ltd., Changzhhou (CN)

( * ) Notice: Subject to any disclaimer, the term of this patent is extended or adjusted under 35 U.S.C. 154(b) by 759 days.

(21) Appl. No.: 12/452,441

(22) PCT Filed: Jun. 10, 2008

(86) PCT No.: PCT/CN2008/001120
§ 371 (c)(1),
(2), (4) Date: Jan. 26, 2010

(87) PCT Pub. No.: WO2009/006780
PCT Pub. Date: Jan. 15, 2009

(65) Prior Publication Data
US 2010/0144902 A1    Jun. 10, 2010

(30) Foreign Application Priority Data

Jul. 6, 2007 (CN) .......................... 2007 1 0093931

(51) Int. Cl.
*A61K 9/14* (2006.01)
*A61K 31/74* (2006.01)
*C07H 7/02* (2006.01)

(52) U.S. Cl.
USPC .................... 424/484; 424/78.27; 536/123.1; 514/54

(58) Field of Classification Search
None
See application file for complete search history.

(56) References Cited

U.S. PATENT DOCUMENTS

| 3,727,310 | A * | 4/1973 | Baker | ............................ 433/80 |
| 6,624,245 | B2 | 9/2003 | Wallace et al. | |
| 7,291,673 | B2 | 11/2007 | Hubbell et al. | |

2004/0225077 A1    11/2004  Gravett et al.
2005/0176620 A1 *   8/2005  Prestwich et al. ................. 514/2
2009/0124540 A1 *   5/2009  Prestwich et al. ............... 514/12

FOREIGN PATENT DOCUMENTS

CN          1756530 A       4/2006
WO     WO 2004/060346 A2    7/2004

OTHER PUBLICATIONS

Qiu et al., "A hydrogel prepared by in situ cross-linking of a thiol-containing poly(ethylene glycol)-based copolymer: a new biomaterial for protein drug delivery," *Biomaterials*, vol. 24, 2003, p. 11-18.
Liu et al., "Reduced postoperative intra-abdominal adhesions using Carbylan-SX, a semisynthetic glycosaminoglycan hydrogel," *Fertility and Sterility*, vol. 87, No. 4, Apr. 2007, pp. 940-948.
Connors et al., "Postoperative Pericardial Adhesion Prevention Using Carbylan-SX in a Rabbit Model," *Journal of Surgical Research*, vol. 140, 2007, pp. 237-242.
International Search Report issued for International Application No. PCT/CN2008/001120 on Sep. 18, 2008 (with translation).

* cited by examiner

*Primary Examiner* — Lakshmi Channavajjala
(74) *Attorney, Agent, or Firm* — Oliff PLC

(57) ABSTRACT

This invention discloses a preparation method for biocompatible rapid-gelating hydrogel. Wherein, hydrogel is formed by rapid chemical-crosslinking using the mixing and chemical-crosslinking reaction under specified conditions between several active compound components. The preparation method comprises the following steps: (1) The solution containing biocompatible thiolated macromolecular derivatives (component A) and biocompatible thiol reactive crosslinking agents (component B) mutually mix to form reactive mixture with specified crosslinking conditions; (2) the reactive mixture forms the hydrogel. The invention also discloses a preparation method for novel rapid-gelating hydrogel spray and an application in medical field. This invention has the advantages of good biocompatibility, no by-products, good stability, convenient use, small amount of raw materials used, suitable for many medical application, etc.

17 Claims, 1 Drawing Sheet

BIOCOMPATIBLE RAPID-GELATING HYDROGEL AND ASSOCIATED PREPARATION METHOD OF SPRAY

TECHNICAL FIELD

This invention relates to preparation methods for hydrogels, especially for biocompatible rapid-gelating hydrogels. The invention is also related to preparation methods for novel rapid-gelating hydrogel spray.

BACKGROUND TECHNOLOGY

Hydrogel, especially those prepared using extracellular matrix, have been widely used in biomedicine field. Compared with the hydrogels prepared by synthetic material, the hydrogels prepared by extracellular matrix have many advantages, for example, being able to simulate the natural environment in organisms, high water content, good permeability, good biocompatibility and adjustable enzyme-degrading property etc (Silva et al., Curr Top Biol Dev, 64, 181, 2004; Drury et al., Biomaterials, 24, 4337, 2003). Even more important, extracellular substance matrix has biological induction effect, which can direct and induce the tissue-specific regeneration. For example, sodium hyaluronate is a natural extracellular matrix polymer, with biological functions such as management of cell adhesion and migration, regulation of cell division and differentiation etc. Sodium hyaluronate with high-molecular-weight can induce the bone marrow stem cells of chick embryo limbs to differentiate into cartilage cells (Kujawa et al., Develop Biol, 114, 519, 1986). Therefore the hydrogels prepared using extracellular matrix has been attracted more and more attention in biomedicine field (especially in tissue engineering field).

In many biomedicine applications, hydrogels are required to be in liquid state in the process of using, but to rapidly form gel after reaching the specified sites and lose their fluidity. Such rapid-gelating hydrogels have great advantages: suitable for any three-dimensional wound with complex shape; having a good adhesion to the wound; being used under endoscope and avoiding the open surgery and so on. So far, researchers have investigated a number of ways to realize the rapid-gelation of hydrogels. For example, water-soluble unsaturated derivatives of polyethylene glycol can be used to prepare gel through photo-initiated crosslinking; the tri-block copolymer solution (Pluronic poloxamer) with a specific composition of polyethylene glycol and polypropylene glycol has gelating behavior induced by temperature change (Leach et al., Am J Obstet Gynecol 162, 1317, 1990); cyanoacrylate can be crosslinked into gel through polymerization and used for tissue gluing; and glutaraldehyde-crosslinked materials of gelatin and so on. Generally speaking, the above hydrogels have various defects, such as poor biocompatibility, poor biodegradability and so on. Rapid-gelating usually needs the crosslinking agents with high activity, but these compounds usually have greater toxicity.

Thiol, a functional group naturally occurring in the biological body, has a good biocompatibility. It has high reactivity which is several orders of magnitude higher than amino group under the same conditions. Therefore, in order to provide rapid chemical cross-linking necessary for rapid-gelation, crosslinkers with high activity (e.g. formaldehyde etc) are needed to crosslink the relatively inert amino group, but this kind of cross-linkers have greater toxicity, and may cause side effects such as tissue inflammation etc., whereas biocompatible crosslinkers with low activity can be used to crosslink thiol to prepare hydrogels with good biocompatibility. Wallace et al dissolved multi-arm (four-arm or twelve-arm) polyethylene glycol thiol derivatives (molecular weight 10,000) into 0.3 mol/L sodium phosphate/sodium carbonate buffer solution (pH=9.6), multi-arm (four-arm or twelve-arm) polyethylene glycol succimide activated derivatives (molecular weight 10,000) in 0.0005 mol/L sodium phosphate buffer solution (pH=6.0) the, and the biocompatibility of hydrogel prepared through the mixing of above two solutions was greatly improved than the hydrogel prepared by using corresponding polyethylene glycol amino derivatives (Wallace et al, U.S. Pat. No. 6,624,245).

Although the method disclosed by Wallace et al is a better way for preparing rapid-gelating hydrogels, there are still many disadvantages (Wallace et al., U.S. Pat. No. 6,624,245). Firstly, N-hydroxyl-succinimide by-products are generated through the chemical crosslinking reaction between multi-arm polyethylene glycol thiol derivatives and multi-arm polyethylene glycol succimide activated derivatives, and they have certain toxicity. Secondly, multi-arm polyethylene glycol succimide activated derivatives and multi-arm polyethylene glycol thiol derivatives solutions adopted by Wallace et al are both unstable, and they need to be freshly prepared. Furthermore, the former solution should be used out within 1 h and the latter is prone to lose activity when contacting with the air and it is difficult to use. Thirdly, both multi-arm polyethylene glycol thiol derivatives and multi-arm polyethylene glycol succimide activated derivatives are very expensive, and only the concentration of the two compounds reaches to as high as 10% w/v or more (usually 20% w/v), respectively, rapid-gelating can be realized, and it is costly.

Invention Content:

One of technical problem to be solved in this invention is to provide a novel preparation method for biocompatible rapid-gelating hydrogel.

The other technical problem to be solved in this invention is to provide a novel preparation method for rapid-gelating hydrogel spray.

Part of terms defined in this invention is as follows:

The biocompatible thiolated macromolecule derivatives refer to the products of biocompatible macromolecules obtained through thiol modification. The mentioned biocompatible thiolated macromolecule derivatives contain at least 3 thiols, with molecular weight of 1,000~10,000,000.

Biocompatible macromolecules refer to polysaccharides (chondroitin sulfate, heparin, heparan, alginic acid, hyaluronic acid, dermatan, dermatan sulfate, pectin, carboxymethyl cellulose, chitosan, etc.), their salt forms (e.g. sodium salt, potassium salt, etc.) and their chemical modified forms (e.g. carboxymethylation modification, hydrophobic modification, etc.), proteins (alkaline type gelatin, acidic type gelatin, alkaline type recombinant gelatin and acidic type recombinant gelatin, etc.) and their chemical modified forms (e.g. carboxylation modification and hydrophobic modification for amino group, etc.), and synthetic macromolecule (polyacrylic acid, polyaspartic acid, polytartaric acid, polyglutamic acid, and polyfumaric acid, etc.) and their salt forms (e.g. sodium salt, potassium salt, etc.) and their chemical modified forms (e.g. carboxymethylation modification, hydrophobic modification, etc.). The above chondroitin sulfate includes many types e.g. A type, B type and C type etc. The above biocompatible macromolecules do not include polyethylene glycol and its derivatives, as well as the oligomeric peptides containing cysteine, etc. (Lutolf et al, Biomacromolecules, 4, 713, 2003).

Thiol modification refers to a chemical reaction process for the introduction of free thiols, and usually includes the following chemical reaction processes: under the activation of carbodiimide, the side-chain carboxyl groups of biocompatible macromolecules react with diamine or dihydrazide containing disulfide bond to generate intermediate products, then disulfide bonds were reduced to give biocompatible thiolated macromolecule derivatives; or the mentioned biocompatible macromolecules' side-chain amino groups were directly modified to be thiol through chemical reaction.

Chemical cross-linking reaction refers to nucleophilic addition reaction and nucleophilic substitution reaction between thiols and thiol-reactive functional groups.

Hydrogel refers to a composite containing lots of water with a 3D crosslinking network structure, and the state between liquid and solid without fluidity. Gelation refers to the process through which the liquid state with fluidity turns into the hydrogel losing the fluidity, and gelating time refers to the time from liquid state with fluidity turns to the hydrogel losing the fluidity.

Alkylidene group refers to —(CH$_2$)n— (n is an integer from 1~15). Preferably n is an integer from 1~8.

Substituted alkylidene group refers to the alkylidene group whose at least one hydrogen atom is substituted by alkyl, hydroxyl, amino, alkoxyl, phenyl, and ester group etc.

Aryl group refers to aromatic phenyl, naphthyl and so on, preferably phenyl.

Polyether group refers to —[(CHR)$_n$O]$_m$—, wherein R is alkyl, n is an integer from 1~10, m is an integer from 1~500. Preferably, R is hydrogen atom, n equals to 2, 3 and 4, respectively.

Alkyl refers to straight-chain or branched-chain alkyl with 1~15 carbon atoms e.g. methyl, ethyl, propyl, isopropyl, butyl, isobutyl, tert-butyl, sec-butyl, amyl, neoamyl, hexyl, heptyl, octyl and so on, preferably to straight-chain or branched-chain alkyl with 1~10 carbon atoms, and preferably methyl, ethyl, propyl, butyl, amyl, hexyl, heptyl and octyl.

Alkoxyl refers to straight-chain or branched-chain alkoxyl with 1~6 carbon atoms e.g. methoxyl, ethoxyl, propoxyl, isopropoxyl, butoxyl, iso-butoxyl, tert-butoxyl, sec-butoxyl, pentyloxyl, neo-pentyloxyl, hexyloxyl, etc., preferably to straight-chain or branched-chain alkoxyl with 1~4 carbon atoms, and preferably methoxyl and ethoxyl.

Ester group refers to —C(O)OR, wherein R is the above low-level alkyl, preferably carbomethoxyl, carbethoxyl, carbopropxyl and carbobutoxyl.

Carboxyl group refers to the carboxyl group (—COOH) and corresponding carboxylate (–COO$^-$A$^+$) after neutralized with alkali. The A$^+$ includes sodium, potassium, lithium-ion, ammonia ion and so on, preferably carboxyl group, carboxylic sodium salt or carboxylic potassium salt.

The connecting group containing an amide bond refers to

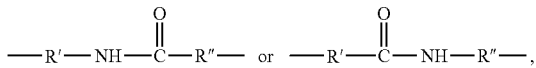

in which R' and R" are the abovementioned alkylidene group, substituted alkylidene group, aromatic group or polyether group.

Polyamide group refers to the group generated by diacid and diamine.

One way to realize the preparation method for biocompatible rapid-gelating hydrogel in this invention includes the following steps:

(1) Component A and component B mix to form reactive mixture with specific crosslinking conditions, component A is a solution containing of biocompatible thiolated macromolecule derivatives, and component B is a biocompatible thiol-reactive crosslinking agent. Wherein, biocompatible thiolated macromolecule derivatives are prepared through thiolation of biocompatible macromolecules. The concentration of component A is less than 8% w/v, the pH value of component A is less than 8.5, and the pH value of component B is higher than that of component A. The thiols in component A reacts with the thiol-reactive functional groups in component B to give chemical cross-linking reaction, the sum of the concentration of biocompatible thiolated macromolecule derivative and the concentration of biocompatible thiolated-reactive cross-linking agent in mentioned reactive mixture is less than 6% w/v. The mentioned specific crosslinking conditions refer to the pH value of reactive mixture solution higher than 7.0.

(2) Reactive Mixture to Form Hydrogel

The basic chemical principle of preparation method for biocompatible hydrogel in this invention is the rapid chemical cross-linking reaction between thiols and biocompatible thiol-reactive functional group under the specific conditions. Generally, there are two active components in this invention: the solution of biocompatible thiolated macromolecule derivatives (component A) and biocompatible thiol-reactive crosslinking agent (component B). The biocompatible thiolated macromolecule derivatives containing at least 3 thiols in component A mix and chemically crosslink with the biocompatible thiol-reactive crosslinking agent containing at least 2 biocompatible thiol-reactive functional groups in component B under specific conditions, and thus this invention can be realized. This invention has the advantages of good biocompatibility, no by-products, good stability, easy to use, and low cost etc.

In this invention, component A refers to the solution containing thiolated biocompatible macromolecule derivatives. Water is the main solvent in the above solution, and also some salt component (e.g. sodium chloride, pH buffer salt component etc.) may be included to adjust osmotic pressure and stabilize solution pH, and also some polar and hydrosoluble components e.g. ethanol etc. may be included.

The biocompatible thiolated macromolecule derivatives used in this invention can be prepared through the thiol modification of biocompatible macromolecule, including direct thiol modification of the side-chain carboxyl group and amino group in biocompatible macromolecule. In addition, the side-chain hydroxyl group and amino group in biocompatible macromolecule can also be firstly conducted with carboxylation modifications to get new biocompatible macromolecule, and then the carboxyl group is thiolated. The thiol modification of biocompatible macromolecules generally includes the several following methods.

The method (I) is amino(hydrazide)/carbodiimide coupling chemical method for side-chain carboxyl group. The preferable way is that the carboxyl group forms intermediate product under the activation of carbodiimide, and then the diamine or dihydrazide containing disulfide bond conducts nucleophilic substitution and generates intermediate product, finally, the disulfide bond is reduced to thiol, and then the biocompatible thiolated macromolecule derivatives are obtained (Shu et al., Biomacromolecules, 3, 1304, 2002; Aeschlimann et al., U.S. Pat. No. 7,196,180 B1). The thiol-protected primary amine also can be used instead of the diamine or dihydrazide containing disulfide bond, and the biocompatible thiolated macromolecule derivatives can be formed after the thiol-deprotection of the obtained intermediate products (Gianolio et al., Bioconjugate Chemistry, 16, 1512, 2005). The above mentioned carbodiimide usually refers to 1-ethyl-3-(3-dimethylamine propyl) carbodiimide hydrochloride. Following is the structure of some amines or hydrazides containing disulfide bond:

(Structural formulas 1–18 of disulfide-containing diamine and dihydrazide compounds)

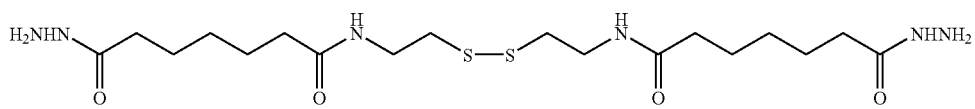

Wherein, (1) is the Cystamine; (2) is the cystine ester; (3) is dithio diphenyl amine; (4) is dithio diethyl dihydrazide; (5) is dithio dipropyl dihydrazide; (6) is dithio dibutyl dihydrazide; (7) is dithio dipropionate diacyl glycine dihydrazide; (8) is dithio dipropionate diacyl alanine dihydrazide; (9) is dithio dipropionate diacyl(hydroxyl-) aminoacetate dihydrazide; (10) is dithio dipropionate diacyl aminopropylate dihydrazide; (11) is dithio dipropionate diacyl aminobutylate dihydrazide; (12) is dithio dibutanate diacyl glycine dihydrazide; (13) is dithio dibutanate diacyl aminopropylate dihydrazide; (14) is dimalonate diacyl cystamine dihydrazide; (15) is disuccinate diacyl cystamine dihydrazide; (16) is di(methyl) succinate diacyl cystamine dihydrazide; (17) is diglutarate diacyl cystamine dihydrazide; (18) is dihexanate diacyl cystamine dihydrazide; (19) is diheptanate diacyl cystamine dihydrazide.

The thiolated macromolecule derivatives prepared by this way generally have the following structures of general formula (I) or general formula (II) (Shu et al., Biomacromolecules, 3, 1304, 2002; Prestwich et al., WO2004/03716; Song et al., Application No. of China Patent of Invention: 200610119414.1).

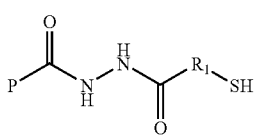

(I)

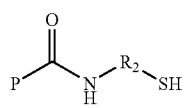

(II)

Wherein $R_1$ and $R_2$ include alkylidene group, substituted alkylidene group, aromatic group, polyether group, amide group, polyamide and so on.

The method (II) is to prepare through the directly reaction of side-chain carboxyl group and carbodiimide containing disulfide bond (e.g. 2,2'-dithio-di(N-ethyl(N'-ethyl carbodiimide)) etc.), and the prepared biocompatible thiolated macromolecule derivatives have the following structure of general formula (III) (Bulpitt et al, U.S. Pat. No. 6,884,788).

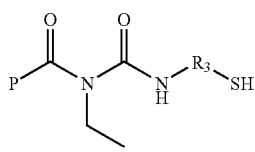

(III)

Wherein $R_3$ include alkylidene group, substituted alkylidene group, aromatic group and so on.

The method (III) is to modify side-chain amino group, the modification generally includes two methods (direct and indirect). Direct modification method refers to the direct modification of the side-chain amino group by introduction of thiol, e.g. the thiol modification of the amino group of collagen using disuccinate diacyl cystamine dicarbonyl-diimidazole activated ester (Yamauchi et al, Biomaterials, 22, 855, 2001; Nicolas et al, Biomaterials, 18, 807, 1997). The thiolated macromolecule derivatives prepared through direct modification method generally have the structure of general formula (IV) or the one similar to general formula (IV).

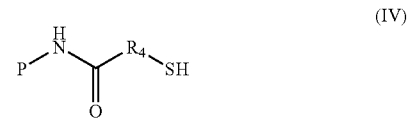

(IV)

Wherein $R_4$ includes alkylidene group, substituted alkylidene group, aromatic group, polyether group, amide group, polyamide and so on.

Indirect modification of amino group in method (III) generally includes two steps. The first step is carboxylation of amino group, and the second step is thiol modification of carboxyl group. Wherein, for the thiolation of carboxyl group in the second step is the same as the aforementioned method (I) and method (II). The thiolated macromolecule derivatives usually have the structure of general formula (V) or the one similar to general formula (VI).

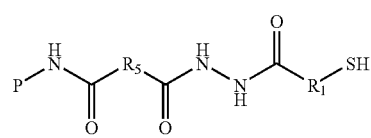

(V)

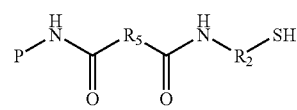

(VI)

Wherein the definition of $R_1$ and $R_2$ are the same with the aforementioned, and $R_5$ includes alkylidene group and substituted alkylidene group etc.

For the biocompatible macromolecule contained both side-chain carboxyl and amino groups, its thiolated derivatives can simultaneously include carboxyl-thiolated structure (general formula (I) or general formula (II) etc.) and the structures by direct or indirect thiol modification of amino groups (general formula (III), (IV), (V) or (VI) etc.) (Song et al, Application No. of China Patent of Invention: 200710036276.5).

The method (IV) is the modification of side-chain hydroxyl. The common method is the carboxylation of hydroxyl under strong alkali condition, then the thiol modification of carboxyl according to the aforementioned method (I) and method (II). For example, the side-chain hydroxyl of macromolecules (cellulose, hyaluronic acid, chitin and chitosan etc.) can all be carboxymethylated, and then amino (hydrazide)/carbodiimide chemical reaction can be used in thiol modification. The prepared thiolated biocompatible macromolecule derivatives generally have the following structure of general formula (VII) or general formula (VIII).

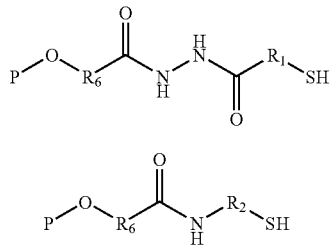

(VII)

(VIII)

Wherein the definition of $R_1$ and $R_2$ are the same as the aforementioned, and $R_6$ includes alkylidene group and substituted alkylidene group etc.

The thiolated derivatives of the biocompatible macromolecule containing both side-chain carboxyl and hydroxyl group can simultaneously include carboxyl-thiolated structure (general formula (I) or general formula (II) etc.) and hydroxyl-thiolated structure (general formula (VII) or general formula (VIII) etc.)

In the above mentioned general formula (I)-(VIII), P refers to the residue of biocompatible macromolecule, wherein side-chain carboxyl, amino group or hydroxyl of biocompatible macromolecules are directly or indirectly modified to thiol, the molecular weight of P is 1,000~10,000,000 in general, and the definition of biocompatible macromolecule is the same as the aforementioned.

In the above mentioned general formula (I)-(VIII), the preferred structures of $R_1$ are alkylidene group —$(CH_2)_m$—, amide group

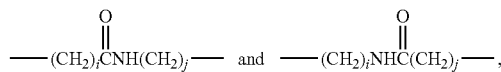

wherein m, i and j are all the integer of 1~15. When m is the integer of 1~3, i is the integer of 1~5, when j is 2 and 3, it is just the specially preferred structure of $R_1$.

In the above mentioned general formula (I)-(VIII), the preferred structures of $R_2$ are aryl group, alkylidene group —$(CH_2)_m$—, and substituted alkylidene group

wherein m is the integer of 1~15, R is methyl, ethyl, propyl and butyl. The specially preferred structures of $R_2$ is the alkylidene groups whose carbon number is 2, R is the above mentioned substituted alkylidene group of methyl and ethyl.

In the abovementioned general formula (I)-(VIII), the preferred structures of $R_3$ are aryl group and alkylidene group —$(CH_2)_m$—, wherein m is the integer of 1~15, the specially preferred structure of $R_3$ is the alkylidene group whose carbon number is 2.

In the abovementioned general formula (I)-(VIII), the preferred structures of $R_4$ are alkylidene group —$(CH_2)_m$—, amide group

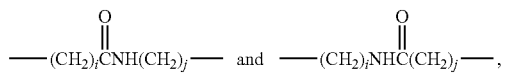

wherein m, i and j are all the integer of 1~15. When m is the integer of 1~3, i is the integer of 1~5, when j is 2 and 3, it is just the specially preferred structure of $R_1$.

In the above mentioned general formula (I)-(VIII), the preferred structures of $R_5$ are alkylidene group —$(CH_2)_m$—, wherein m is the integer of 1~15, when m is the integer of 1~8, it is just the specially preferred structure of $R_5$.

In the abovementioned general formula (I)-(VIII), the preferred structures of $R_6$ is alkylidene group —$(CH_2)_m$—, wherein m is the integer of 1~15, when m is the integer of 1~5, it is just the specially preferred structure of $R_5$.

The structures of part of preferred biocompatible thiolated macromolecule derivatives adopted in this invention are shown as follows:

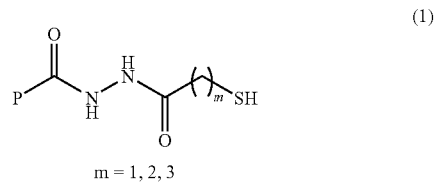

(1)

m = 1, 2, 3

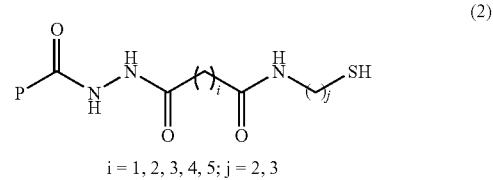

(2)

i = 1, 2, 3, 4, 5; j = 2, 3

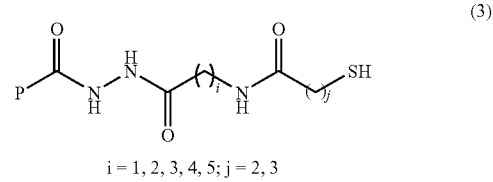

(3)

i = 1, 2, 3, 4, 5; j = 2, 3

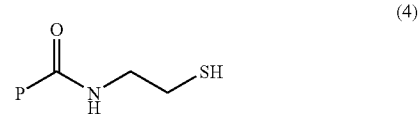

(4)

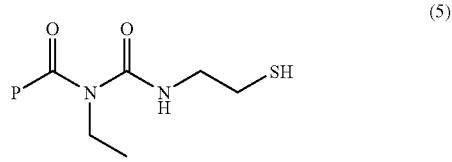

(5)

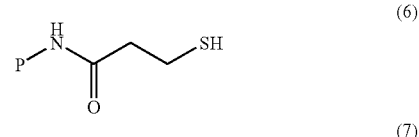

(6)

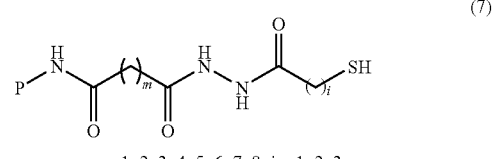

(7)

m = 1, 2, 3, 4, 5, 6, 7, 8; i = 1, 2, 3

(8)
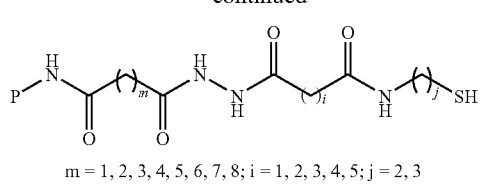
m = 1, 2, 3, 4, 5, 6, 7, 8; i = 1, 2, 3, 4, 5; j = 2, 3

(9)
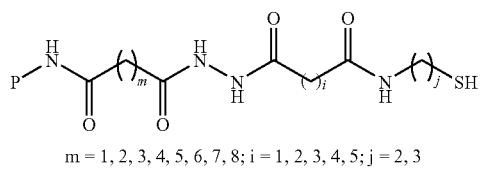
m = 1, 2, 3, 4, 5, 6, 7, 8; i = 1, 2, 3, 4, 5; j = 2, 3

(10)
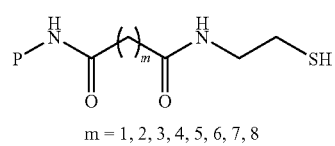
m = 1, 2, 3, 4, 5, 6, 7, 8

(11)
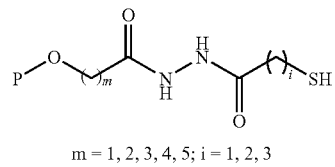
m = 1, 2, 3, 4, 5; i = 1, 2, 3

(12)
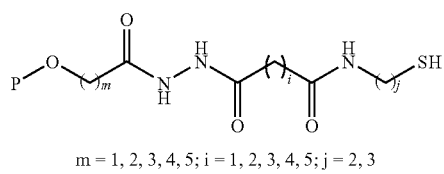
m = 1, 2, 3, 4, 5; i = 1, 2, 3, 4, 5; j = 2, 3

(13)
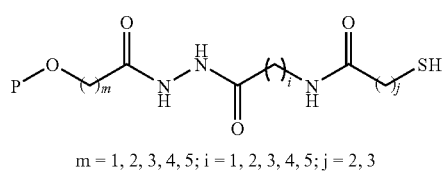
m = 1, 2, 3, 4, 5; i = 1, 2, 3, 4, 5; j = 2, 3

(14)
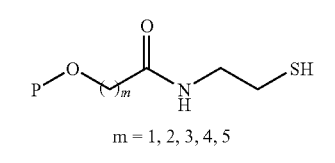
m = 1, 2, 3, 4, 5

Wherein structure formula (1), (2) and (3) belong to the specially preferred biocompatible thiolated macromolecule derivatives of general formula (I); structure formula (4) belongs to the specially preferred biocompatible thiolated macromolecule derivatives of general formula (II); structure formula (5) belongs to the specially preferred biocompatible thiolated macromolecule derivatives of general formula (III); structure formula (6) belongs to the specially preferred biocompatible thiolated macromolecule derivatives of general formula (IV); structure formula (7), (8) and (9) belong to the specially preferred biocompatible thiolated macromolecule derivatives of general formula (V); structure formula (10) belongs to the specially preferred biocompatible thiolated macromolecule derivatives of general formula (VI); structure formula (11), (12) and (13) belong to the specially preferred biocompatible thiolated macromolecule derivatives of general formula (VII); structure formula (14) belongs to the specially preferred thiolated biocompatible macromolecule derivatives of general formula (VIII).

For the biocompatible thiolated macromolecule derivatives synthesized by using the biocompatible macromolecule simultaneously having carboxyl, amino group and hydroxyl, their specially preferred structures may have one or more structures as structure formula (1)-(14). For example, hyaluronic acid simultaneously has carboxyl and hydroxyl, hydroxyl can be modified to carboxyl by carboxymethylating, then amino (hydrazide)/carbodiimide chemical reaction is conducted for thiol modification, the prepared thiolated hyaluronic acid derivatives simultaneously have the structure as shown in structure formula (1), (2) or (3) and structure formula (11), (12) or (13) (Prestwich et al., PCT Int. Appl. WO 2005/056608). Gelatin has both carboxyl and amino group, the amino can react with diacid anhydride to introduce carboxyl, then amino (hydrazide)/carbodiimide chemical reaction is conducted for thiol modification, the synthesized thiolated gelatin derivatives simultaneously have the structure as shown in structure formula (1), (2) or (3) and structure formula (7), (8) or (9) (Song et al., Application No. of China Patent of Invention: 200710036276.5).

The component B used in this invention is biocompatible thiol-reactive crosslinker which contains at least two thiol-reactive functional groups. In general, thiol-reactive functional groups usually contain maleimide, vinyl sulfone, α,β-unsaturated acrylate, α,β-unsaturated methacrylate, halogenated propionate, halogenated propionamide, dithiopyridine and N-hydroxyl succinimide activated ester and so on. Wherein the functional groups e.g. maleimide, vinyl sulfone, iodo-propionate, iodo-propionamide, and dithio-pyridine etc. have higher thiol-reactivity. The reaction between above mentioned functional group and thiol can be divided into 3 types: (1) addition reaction between thiol and unsaturated double bond, wherein the functional groups belong to this reaction type including maleimide, vinyl sulfone, α,β-unsaturated acrylate, α,β-unsaturated methacrylate and so on; (2) substitution reaction of thiol, wherein the functional groups belong to this reaction type including iodo-propionate, bromo-propionate, chloro-propionate, iodo-propionamide, bromo-propionate, chloro-propionate, and dithio-pyridine etc. (3) thioesterification reaction, wherein the functional groups belong to this reaction type including the activated esters of all kinds of carboxylic acids e.g. N-hydroxyl succinimide activated ester and so on. The reaction equation between thiol and the above mentioned thiol-reactive functional groups are shown as follows:

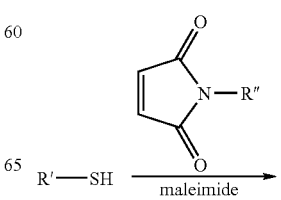

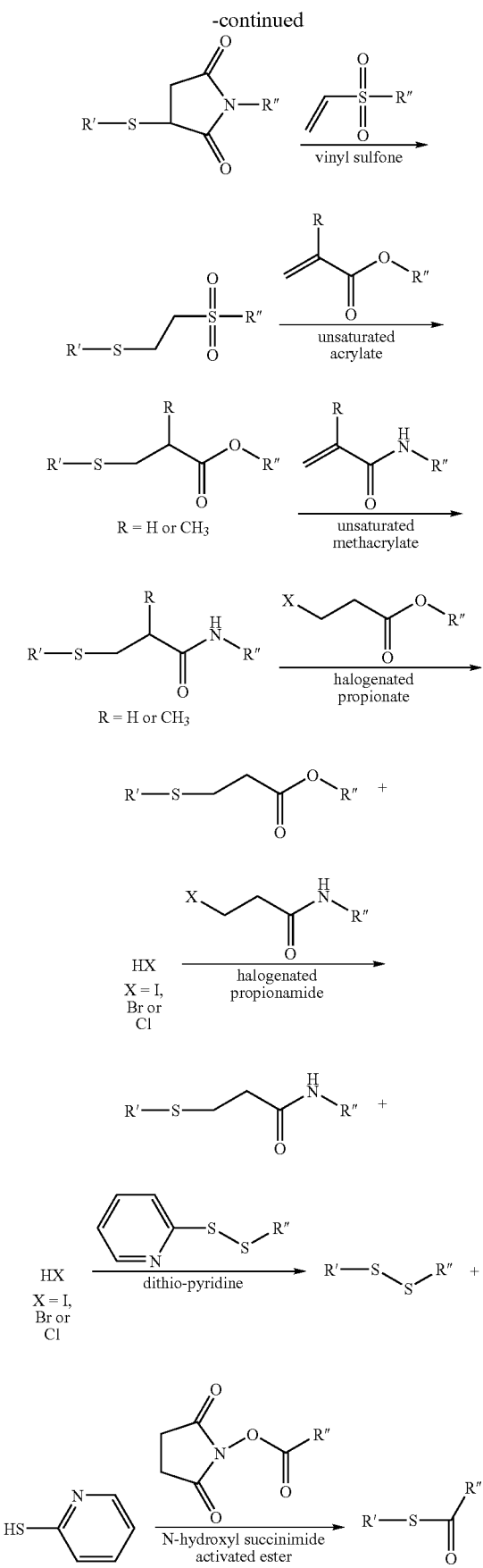

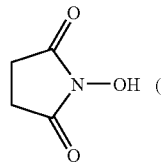

In the above thiol-reactive functional group, N-hydroxyl succinimide activated ester has the stronger reactivity, and can react with both amino group and thiol without selectivity. Hence, it has considerable toxic and side effects. At the same time, a byproduct of N-hydroxyl-succinimide is generated when N-hydroxyl succinimide activated ester reacts with thiol, which may result in the producing of toxic and side effects. In addition, the thioester bonds formed between N-hydroxyl succinimide activated ester and thiol are not stable and apt to hydrolyse, which seriously restrict their application in medicine field. Although Wallace et al (U.S. Pat. No. 6,624,245) has ever used polyethylene glycol succimide activated ester derivatives to crosslink polyethylene glycol thiol derivatives, but because of the above serious disadvantages, this invention did not adopt N-hydroxyl succinimide activated ester as the thiol-reactive functional group. The reaction between dithio-pyridine and sulfhydryl also generates a byproduct, and it may also produce toxic and side effects, therefore, the present invention did not adopt either.

The thiol-reactive functional groups adopted by this invention including maleimide, vinyl sulfone, $\alpha,\beta$-unsaturated acrylate, $\alpha,\beta$-unsaturated methacrylate, $\alpha,\beta$-unsaturated acrylamide, $\alpha,\beta$-unsaturated methyl acrylamide, iodo-propionate, bromo-propionate, chloro-propionate, iodo-propionamide, bromo-propionate, and chloro-propionate etc. When iodo-propionate, bromo-propionate, chloro-propionate, iodo-propionamide, bromo-propionate, and chloro-propionate etc functional groups react with thiol, though byproduct are also generated, these byproducts are halogenated acids which can form chloride ion, bromide ion, or iodide ion under physiological condition, therefore, they also have good biocompatibility. Wherein halogenated propionate has better thiol-reactivity than corresponding halogenated propionamide, but its stability is worse; iodo-propionate (or iodo-propionamide) has better thiol-reactivity than corresponding bromo functional groups, but its stability is somewhat less; the thiol-reactivity of chloro-propionate (or chloro-propionamide) is the lowest, but its stability is better.

The preferred thiol-reactive functional groups in this invention are maleimide, vinyl sulfone, $\alpha,\beta$-unsaturated acrylate, $\alpha,\beta$-unsaturated methacrylate, $\alpha,\beta$-unsaturated acrylamide, $\alpha,\beta$-unsaturated methyl acrylamide, etc. These functional group not only have good biocompatibility, but also do not generate by-products when reacts with thiol. The specially preferred thiol-reactive functional groups in this invention are vinyl sulfone, $\alpha,\beta$-unsaturated acrylate, $\alpha,\beta$-unsaturated methacrylate, $\alpha,\beta$-unsaturated acrylamide, and $\alpha,\beta$-unsaturated methyl acrylamide, etc. They not only have good biocompatibility, but have greatly improved stability than N-hydroxyl succinimide activated ester.

The component B containing more than one thiol-reactive functional group adopted by this invention is usually the derivatives of polyethylene glycol (PEG) containing at least two aforementioned thiol-reactive functional groups e.g. two-arm, three-arm, four-arm, eight-arm or multi-arm PEG derivatives, and they have the following typical chemical structures:

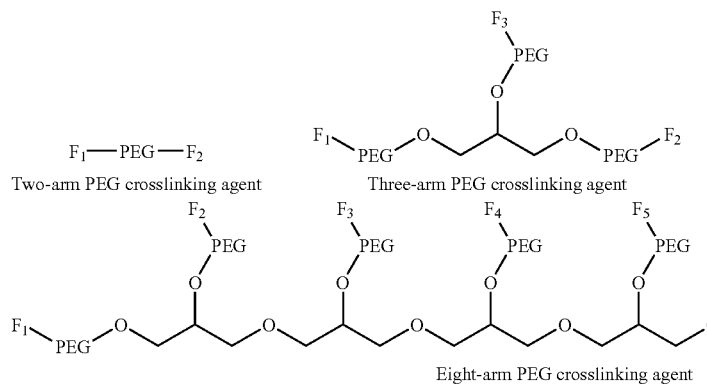
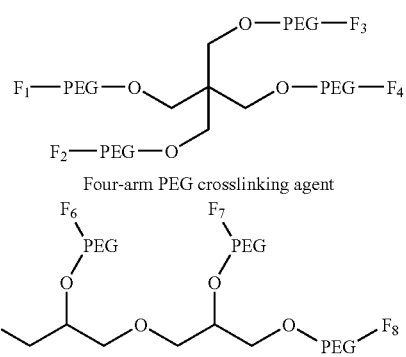

Wherein $F_1$, $F_2$, $F_3$, $F_4$, $F_5$, $F_6$, $F_7$ and $F_8$ are the aforementioned thiol-reactive functional groups e.g. maleimide, vinyl sulfone, α,β-unsaturated acrylate, α,β-unsaturated methacrylate, α,β-unsaturated acrylamide, α,β-unsaturated methyl acrylamide, iodo-propionate, bromo-propionate, chloro-propionate, iodo-propionamide, bromo-propionate, and chloro-propionate etc., they can be the same, some of the same or totally different chemical structures. PEG refers to the chain segment with $CH_2CH_2O$ repeated unit, and the molecular weight is from 100 to 1000000. Preferably, $F_1$, $F_2$, $F_3$, $F_4$, $F_5$, $F_6$, $F_7$ and $F_8$ are maleimide, vinyl sulfone, α,β-unsaturated acrylate, α,β-unsaturated methacrylate, α,β-unsaturated acrylamide, α,β-unsaturated methyl acrylamide etc functional groups, optimally, they are vinyl sulfone, α,β-unsaturated acrylate, α,β-unsaturated methacrylate, α,β-unsaturated acrylamide, α,β-unsaturated methyl acrylamide etc. functional groups.

Take two-arm PEG as an example, the common crosslinking agents was adopted by this invention including PEG dimaleimide, PEG divinyl sulfone, PEG di(methyl)acrylate, PEG di(methyl)acrylamide, PEG dihalogeno-propionate, and PEG dihalogeno-propionamide etc. The chemical structures are shown as follows:

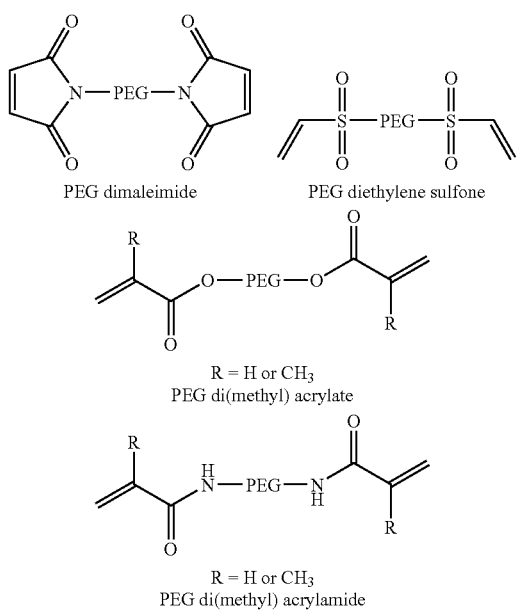

-continued

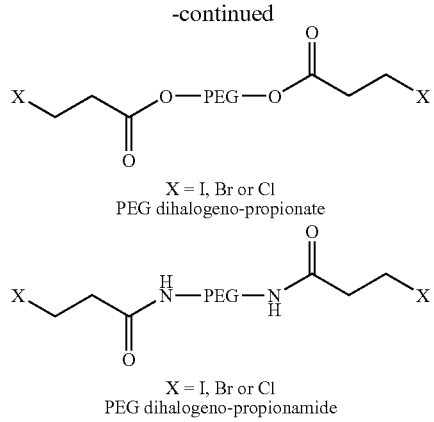

The first step of one way to realize the preparation method for novel biocompatible rapid-gelating hydrogel in this invention is to prepare the reactive mixture solution with specific crosslinking conditions where the key point is to adjust the property of component A and component B to make the pH value of reactive mixture solution to be alkalescence or alkality. The preferable pH value of reaction mixture solution is 8.0~12.0, especially preferably 8.5~10.5.

As stated before, both the selected component A and component B in this invention have good biocompatibility, meanwhile, the chemical cross-linking reaction between thiol and thiol-reactive functional group also has good biocompatibility, which provides solid basis for good biocompatibility of this invention. In addition, to achieve rapid-gelation, other important parameters e.g. concentration of component A and component B, solution pH value, and temperature etc. should be optimized as well.

In this invention, the adopted temperature is generally 0~50° C. The increase of the temperature of chemical crosslinking reaction can accelerate the gelating rate. During practical application, the preferred temperature is usually between 10~40° C. The most common temperature in this invention is room temperature which is around 25° C.

In the preparation method for rapid-gelating hydrogel disclosed by Wallace et al, to realize rapid-gelating, the pH value of the used multi-arm PEG thiol derivative solution must be in stronger alkali condition (usually pH value is 9.6), and the solution's concentration must be more than 10% w/v (Wallace et al, U.S. Pat. No. 6,624,245). However, the thiol is unstable under alkalic condition, especially under stronger alkalic condition, and apt to form disulfide bond and then loses the reactivity. Therefore, the multi-arm PEG thiol derivative should be freshly prepared and is apt to lose reactivity when contacted with air, which is difficult to use. In this invention, for convenient use, the component A solution does not need to be prepared freshly, usually biocompatible thiolated macromolecule derivative is first used to prepare component A solution which can be stored under frozen at low-temperature after sterilization and be readily defrosted before use. Compared with the multi-arm PEG thiol derivative (molecular weight 10,000, at most 12 thiol/10,000 molecular weight chain segments) adopted by Wallace et al (Wallace et al, U.S. Pat. No. 6,624,245), the biocompatible thiolated macromolecule derivative adopted in this invention usually have greater molecular weight (usually between 10,000~1,000,000) and higher thiol content (may be as much as 100 thiol/10,000 molecular weight chain segments) (Shu et al, Biomacromolecules, 3, 1304, 2002). Therefore, the component A in the invention is very unstable under stronger alkalic condition, and the disclosed method by Wallace et al can not be used to realize rapid-gelation (Wallace et al, U.S. Pat. No. 6,624,245).

In order to overcome the unstable defect of thiolated derivatives under stronger alkaline conditions, the pH value of component A adopted in this invention is usually below 8.5, preferably ≤7.0, at this time the solution has a certain stability. A more preferable pH range is 2.5~7.0, under which the solution has good stability, and can be stored for more than one year at minus 30° C., it can be stored for more than 2 hours when the solution contacts the air at room temperature and stored for at least 5 hours without contact with the air at room temperature. The specially preferred pH range is 3.5~6.0, under this condition the thiol are very stable, while the hydrolysis of biocompatible thiolated macromolecule derivatives by acids is mainly avoided. Under this specially preferred condition, the stability of component A adopted in this invention is essentially improved when compared with the multi-arm PEG thiol derivative solution adopted by Wallace, etc. (Wallace et al., U.S. Pat. No. 6,624,245) which is apt to be deactivated. It can be stored for more than 2 years at minus 30° C., even if contacting with the air at room temperature, it can be stored for more than 24 hours.

In this invention, the above mentioned conditions guarantee the long-term storage and good stability of component A before use. Also alkaline solution or alkaline substances can be added into the above component A before component A mixs with component B, to raise the pH value of component A (e.g. higher than 8.5), which is immediately mixed with component B to prepare hydrogel.

In this invention, the concentration of biocompatible thiolated macromolecule derivative in component A is usually less than 8.0% w/v, preferred concentration 0.5~5.0% w/v, and especially preferred 0.8~3.0% w/v. While in preparation method for rapid-gelating gel published by Wallace et al, in order to achieve rapid-gelating, the concentration of multi-arm PEG thiol derivative solution must be more than 10% w/v (usually 20% w/v) (Wallace et al., U.S. Pat. No. 6,624,245). When the concentration of component A is expecially preferred, the consumption of biocompatible thiolated macromolecule derivative in this invention is decreased by 80~90%, which greatly reduces cost.

In this invention, the component A can be aqueous solution, in which sodium chloride, buffer salt and other ingredients can be added. Usually the buffer salt with a low concentration (e.g. 0.0005 mol/L weakly acidic sodium phosphate buffer solution) can stabilize the pH value of the solution, while sodium chloride etc. can adjust the osmotic pressure of the solution.

In this invention, the adopted biocompatible thiol-reactive cross-linking agents are very stable in solid state at low temperature, and usually it can be stored for a long term at minus 30° C. (more than two years); at the same time, they are readily to be dissolved, so the component B can be freshly prepared. The pH value of component B is higher than that of component A, and the pH value of component B is generally higher than 8.0, and usually ≥8.5, and its stable time at room temperature is generally more than 2 hours. For example, the polyethylene glycol diacrylate solution (pH 9.6) adopted in this invention can be stored at room temperature for 4 hours having no influence on the gelating time. In addition, under the same conditions, for polyethylene glycol dimethacrylate solution, polyethylene glycol diacrylamide solution and polyethylene glycol dimethyl acrylamide solution adopted in this invention, their stability are improved one by one, and furthermore they are all more stable than polyethylene glycol diacrylate solution. In this invention, the pH value of component B is preferred 8.0~12.0, especially preferred 8.5~10.5.

The component B adopted in this invention has great advantages. In the preparation method for rapid-gelating gel published by Wallace et al, the adopted cross-linker (multi-arm polyethylene glycol succimide activated derivatives) is very unstable at both acidic and alkaline conditions, and it must be dissolved into 0.0005 mol/L sodium phosphate buffer solution to get weakly acidic solution (pH 6.0). But even under this optimal condition, the solution stability is still very poor, it needs freshly prepared and must be used up within an hour.

In this invention, the concentration of biocompatible thiol-reactive cross-linking agent in component B is usually less than 10% w/v, preferred 0.5~8.0% w/v, especially preferably 0.8~4.0% w/v. In the methods disclosed by Wallace et al., in order to achieve rapid-gelating, the concentration of the adopted cross-linking agent (multi-arm polyethylene glycol succimide activated derivatives) solution must be more than 10% w/v (usually 20% w/v) (Wallace et al., U.S. Pat. No. 6,624,245). In this invention, when the especially preferred concentration of component B is used, the consumption of cross-linking agent is reduced by 60~96%, which significantly reduces cost.

In this invention, component B usually uses alkaline buffer solution as the solvent, sodium chloride and other ingredients can also be added to adjust solution osmotic pressure. The concentration of the adopted buffer solution is generally higher, e.g. 0.3 mol/L sodium phosphate/sodium carbonate buffer solution (pH 9.0~10.0) (adjust pH to preset value by adding 0.3 mol/L sodium dihydrogen phosphate solution into 0.3 Mol/L sodium carbonate solution), etc. Because the biocompatible cross-linking agent in component B usually does not change the solution acidity, the pH value of the buffer solution determines the pH value of component B solution.

When component A and component B are mixed, the reactive mixture with a special cross-linking condition is formed. At room temperature, the pH value of reactive mixture solution mainly determines the cross-linking and gelating speed, and the increase of pH value accelerates the cross-linking and gelating process. The pH value of the reactive mixture solution is usually higher than 7.0, preferably 8.0~12.0, especially preferably 8.5~10.5.

The pH value of reactive mixture is determined when component A mixed with component B, or may be regulated by adding acidic or alkaline solution. The pH value of reactive mixture solution is determined by the properties (e.g. solvent type, concentration and pH value of buffer solution etc.) of initial component A and component B. The solution of component A and component B may contain pH-buffering substance with different concentrations or without contain pH-buffering substance, and other polar and hydrophilic material can also be added. The adjustment of the properties of initial component A and component B solution can regulate the acidity or alkalinity of the reactive mixture to reach the specified pH value. For example, when component A is the aqueous solution of pH=6.0, the solvent of component B is 0.3 mol/L sodium phosphate/sodium carbonate buffer solution of pH=9.6, the reactive mixture solution of component A and component B is alkaline, and its pH value is usually 9.0~9.6; the increase of the solvent pH value of component B can raise the pH value of reactive mixture solution, on the contrary, the pH value of reactive mixture may decrease.

In this invention, acid or base solution (e.g. 0.2 mol/L sodium hydroxide solution, etc.) with a certain concentration can also be added into the reactive mixture solution, or into the component A or component B solution before mixing, or into the reactive mixture solution during the mixing between component A and component B, to adjust the pH value of reactive mixture to the specified value, so as to realize appropriate gelating speed. However, this step is usually not required, and to adjust the properties of initial component A solution and component B solution can realize this invention.

In the invention, the amount of both biocompatible thiolated macromolecule derivatives and biocompatible thiol-reactive cross-linking agent used in this invention are relatively low, the sum of the two concentrations in reactive mixture is generally less than 6% w/v, usually 0.8~3.0% w/v.

Selecting appropriate biocompatible thiolated macromolecule and biocompatible thiol-reactive cross-linking agent, regulating the solution property of component A and component B, and selectively adding acid/base to further regulate the pH value of reactive mixture solution, the gelating time can be regulated within several seconds to several minutes (even dozens of minutes) to suit for different medical applications. For example, this invention can be conveniently used for rapid-gelating hydrogel spray for treatment of postoperative complications of adhesion and realize the gelating time of less than 1 minute.

Another way to realize the preparation method for novel biocompatible rapid-gelating hydrogel by the invention includes the following 3 steps:

(1) component A and component B mix to form the reactive mixture of specific cross-linking condition, component A is a solution containing biocompatible thiolated macromolecule derivatives, component B is a biocompatible thiol-reactive cross-linking agent, component B is a solid or a solution, of which biocompatible thiolated macromolecule derivative is prepared by the thiol modification of biocompatible macromolecule, the concentration of component A is less than 8% w/v, the pH value of component A is less than 8.5, the thiol in component A and the thiol-reactive functional group in component B conduct chemical cross-linking reaction, and mentioned specified cross-linking condition refers to the pH value of reactive mixture solution ≤7.0;

(2) Adjust the pH value of reactive mixture solution to a specified alkaline range.

(3) The reactive mixture forms hydrogel.

The first step of this way is to prepare the reactive mixture solution with good stability, wherein the key is to control the pH value of the reactive mixture to be weakly acidic. In this way, its difference from the aforementioned method is that the biocompatible cross-linking agent (component B) can be in solid state, or in the form of solution having weakly alkaline, neutral or weakly acidic, and the pH value of the reactive mixture solution formed by mixing between component A and component B is ≤7.0, preferably 2.5~6.0, now the reactive mixture solution has good stability, and can be stored for more than 1 hour in contact with air at room temperature. The especially preferred pH range is 3.5~5.0, and the reactive mixture solution has good stability, and usually can be stored for more than 4 hour in contact with air at room temperature.

The second step of this way is to add alkali or alkaline buffer solution (e.g. 0.2 mol/L sodium hydroxide solution/ potassium hydroxide solution, phosphate of pH=9.0~12.0, carbonate buffer solution and so forth) into the reactive mixture solution with relatively good stability, and the pH value of the solution is adjusted to be weakly alkaline or alkaline, with the preferred pH value 8.0~12.0, and especially preferred pH value 8.5~10.5.

The third step of this way is that under the above mentioned condition, component A and component B in the reactive mixture solution rapidly form hydrogel. The adopted biocompatible thiolated macromolecule derivatives and biocompatible thiol-reactive cross-linking agent by this route are the same as those in the aforementioned route, and the other conditions of the route are the same as the foregoing route.

In this invention, to select appropriate biocompatible thiolated macromolecule and biocompatible thiol-reactive cross-linking agent, regulate the property of component A and component B, and regulate the pH value of reactive mixture solution to be specified value, the gelating time can be regulated within several seconds to several minutes (even dozens of minutes) to suit for different medical applications. For example, the invention can be conveniently used for rapid-gelating hydrogel spray for treatment of postoperative complications of adhesion and realize the gelating time of less than 1 minute.

The biocompatible thiolated macromolecule in component A adopted in this invention usually has high molecular weight and thiol content, its molecular weight is usually between 10,000~1,000,000, and the thiol content can be as high as more than 100 thiol/10,000 molecular weight chain segments, that is, each biocompatible thiolated macromolecule with molecular weight 50,000 have 500 thiols. Compared with the disclosed polyethylene glycol thiol derivatives and cysteine-containing oligopeptides (Wallace et al., U.S. Pat. No. 6,624,245; Gravett et al., US2004/0225077A1; Qiu et al., Biomaterials, 24, 11, 2003; Hubbell et al., US2003/0220245A1, Lutolf et al., Biomacromolecules, 4, 713, 2003), the thiol content in biocompatible thiolated macromolecules adopted in this invention is increased more than 8 times at least, and the molecular weight has also been greatly increased. Therefore, under the same conditions, the ability of biocompatible thiolated macromolecules adopted in this invention to conduct chemical cross-linking to form gel has been greatly improved, and the performance (e.g. mechanical strength, stability, permeability, etc.) of the gel have also been greatly improved. In the above-mentioned reports involving polyethylene glycol thiol derivatives and cysteine oligopeptides etc., only very high concentration (usually more than 10% w/v) can realize rapid crosslinking gelation, moreover, their solutions are weakly alkaline or must be alkaline, their stability are poor, and they must be freshly prepared and can not contact with air; at the same time, the concentration of the adopted cross-linking agents is also very high (usually more than 10% w/v), the water content in prepared hydrogel is generally less than 90%, usually 80% or so. In contrast, in this invention, the rapid crosslinking gelation can be realized even in very small quantities of biocompatible thiolated macromolecule and biocompatible thiol-reactive cross-linking agent used in this invention, the Water content in prepared hydrogel is generally more than 94%, usually higher than 97%, and the hydrogel has better permeability and biocompatibility. In addition, the biocompatible thiolated macromolecules in component A adopted in this invention are usually prepared using extracellular matrix (e.g. hyaluronic acid, etc.), and they retain the extracellular matrix-specific biological functions e.g. promoting trauma healing, directing and inducing the specific regeneration of tissues etc.

The biocompatible thiolated macromolecule in component A adopted by this invention is very unstable under stronger alkaline condition, and the method disclosed by Wallace et al (Wallace et al., U.S. Pat. No. 6,624,245) cannot be used to realize rapid-gelating. For example, hyaluronic acid thiolated derivative is extremely apt to form disulfide bond under strong alkaline condition, and thereby lose activity (Shu et al., Biomacromolecules, 3, 1304, 2002). Generally speaking, if the pH value of component A in this invention is greater than 8.5, the solution is very unstable and very inconvenient for use, and loses the practical value. For this reason, the component A in this invention is usually stored under near-neutral or slightly acidic condition, to significantly improve long-term storage stability of component A and its stability during use. But on the other hand, the realization of rapid-gelating further depends on the higher pH value (relatively strong alkaline) of the reactive mixture. Therefore, in one of routes to realize this invention component B usually has relatively strong alkaline, the pH value of component B must be greater than that of component A, so that the reactive mixture of component A and component B can have higher pH value (relatively strong alkaline). At the same time, the biocompatible thiol-reactive cross-linking agent in component B adopted by this invention must have good stability under various conditions (including relatively strong alkaline). By regulating the solution property of component A and component B and selectively adding acid/base to further regulate the pH value of reactive mixture solution, this invention can be realized.

In another preparation route of this invention, the solution property of component A and component B can also be adjusted to let the reactive mixture of component A and component B under weakly acidic condition, which can not only improve long-term storage stability of component A as well as component B and their stability during use, but also significantly improve the stability of reactive mixture during use, and then alkali can be added to further adjust the pH value of reactive mixture to relatively strong alkaline, to realize rapid-gelation.

Currently, although there are a small number of reports disclosing the hyaluronic acid thiolated derivatives, chondroitin sulfate thiolated derivatives and gelatin thiolated derivatives crosslinked by polyethylene glycol diacrylate (or polyethylene glycol divinyl sulfoxide), the adopted methods are all the same i.e. dissolving polyethylene glycol diacrylate (or polyethylene glycol divinyl sulfoxide) and thiolated derivatives into buffer solution, respectively, and adjusting the pH value of the two solutions to be the same near-neutral (usually 7.4), and then mixing the two solutions to prepare hydrogel. In this approach, however, it's difficult to achieve rapid-gelation. To simultaneously increase the pH value of the two solutions (e.g. 8.5 above) can accelerate the gelating process, but now the thiolated derivative solution is unstable, it may lose activity after several hours (usually around 0.5~4 hours), at room temperature even without exposure to the air, difficult for long-term storage, and it's also difficult for large-scale industrial production, and difficult to use. For example, Liu et al (Liu et al, Fertility & Sterility, 87, 940, 2007) reported the application of Carbylan-SX (polyethylene glycol diacrylate crosslinked hyaluronic acid thiolated derivatives) hydrogel spray in prevention and treatment of postoperative adhesion. The adopted approach is to dissolve polyethylene glycol diacrylate and hyaluronic acid thiolated derivatives into buffer solution, respectively, and adjust the pH value of the two solutions to 7.4, sterilize by filtration, then mix two solutions, the viscosity of the mixture solution may be gradually improved about 5 minutes later; now spray the solution to the surface of wound tissue by spraying device. However, this approach has many obvious defects, e.g. long gelating time and difficult to control gelating process as well as difficulty in selecting the time for spraying etc. Spraying can only be realized in a very narrow time range when the viscosity of mixed solution is very high and also the solution has not lost fluidity yet. When its viscosity is not high enough, the solution is apt to flow away from the surface of wound tissue; but when its viscosity is too high, the solution cannot be sprayed. Connors et al. also applied the same Carbylan-SX and its preparation method in prevention and treatment of postoperative pericardial adhesion (Connors et al., Surg Res, 140, 237, 2007), but the same above defects also exist.

In addition, this invention also provides a novel preparation method for biocompatible rapid-gelating hydrogel spray, which is a method for applying the aforementioned preparation method for biocompatible rapid-gelating hydrogel in this invention to spray form of biocompatible rapid-gelating hydrogel.

In this method, the various spraying equipment suitable for multi-component mixed reactions can be adopted. The more commonly used spraying equipments include Spray Set for TISSEEL Fibrin Sealant (Baxter AG, USA), FibriJet (Micromedics Inc. USA) and so on. FibriJet series include ordinary atomization applicator kit and gas assisted atomization applicator kit. The ordinary atomization applicator kit of FibriJet series is suitable for low viscosity solutions, and the applicator tips are easily blocked and it's difficult to use. The structural schematic diagram of gas assisted atomization equipments of FibriJet series is shown in FIG. 1, including syringes 2A and 2B, syringe plunger clip 1, syringe holder 3, four-way applicator tip 4 and a pressurized gas inlet tubing 5. Syringes 2A and 2B are used for loading two components, respectively, which are squeezed out through four-way applicator tip 4, respectively, for atomization and mixing (or atomization following extrusion and mixing), then the gel forms after the solution is sprayed on the object's surface (e.g. trauma surface). The spray tip can also be added to improve atomization effect by connecting with the four-way applicator tip 4.

The key component of gas assisted atomization applicator kit of FibriJet series is the four-way applicator 4 (as shown in FIG. 2). Two inlets connect with two syringes 2A and 2B, respectively, and used for loading two components, one inlet (pressurized gas inlet pipe 5) connects with pressure gases (air or other gases), two components are extruded at the outlet, respectively, atomized and mixed under the effect of pressurized gas, then the gel formed after the solution is sprayed on the object's surface. The higher the pressure of pressurized gas is, the better the atomization effect is, however, too high gas pressure may cause harm to the human body. Usually the adopted gas pressure range is 1~10 atmospheric pressure. When the gas pressure is relatively low and approximate to one atmospheric pressure, the atomization is not enough and relatively large liquid particles are formed, and the mixing is not very homogeneous; when the gas pressure is increased to 1.7 atmospheric pressure or so, very small liquid can be formed by atomizing, and the mixing is very homogenous. Component A and component B in one route of preparation method for biocompatible rapid-gelating hydrogel in this invention can be filled into two syringes, respectively, to prepare rapid-gelating hydrogel spray. Meanwhile, the spraying can be realized by the other route regarding to the preparation method for biocompatible rapid-gelating hydrogel of this invention, wherein the reactive mixture formed by the mixing between component A and component B is filled into one syringe, while alkali or alkaline buffer solution is filled into the second syringe, then the two were extruded at the outlet, respectively, then atomized and mixed under the effect of pressurized gas, thus the rapid-gelating hydrogel spray is prepared.

ILLUSTRATION OF DRAWINGS

THE BEST WAY TO REALIZE THE INVENTION

Figure 1:
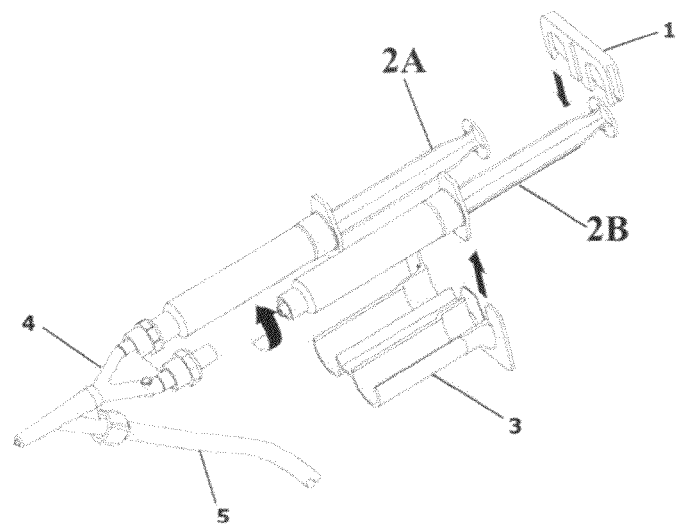
FIG. 1 is part of structural schematic diagram of atomization applicator kit of FibriJet series used for multi-component mixing reaction, wherein, 1 is a syringe plunger clip, 2 is syringes, 3 is a syringe holder, 4 is a four-way applicator tip, and 5 is a pressurized gas inlet pipe.
Figure 2:
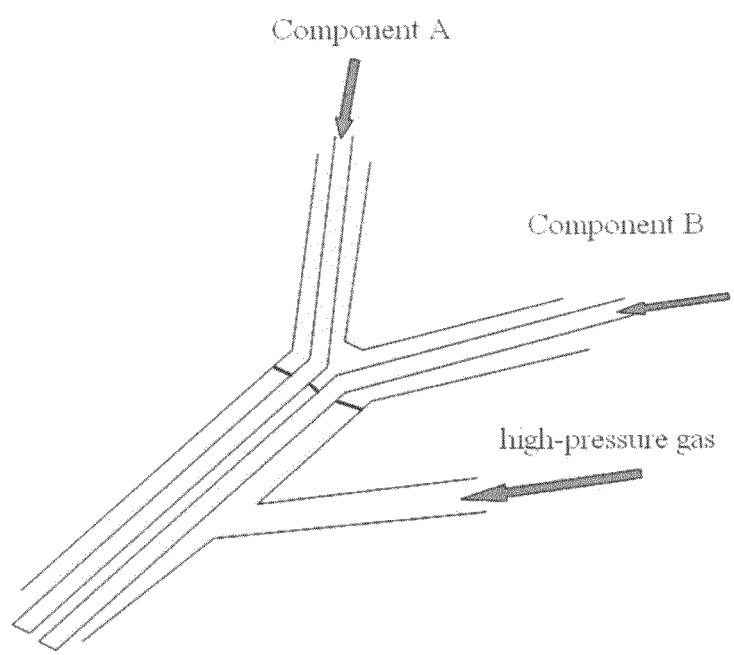
FIG. 2 is the structural schematic diagram of the four-way applicator tip in FIG. 1.

The following examples may enable the technical staff in this field to have a comprehensive understanding of the invention, but do not in any way limit the present invention.

Example 1

Preparation of Thiolated Hyaluronic Acid (HA-DTPH)

The method reported by Shu et al (Shu et al., Biomacromolecules, 3, 1304, 2002) was used.

20 g Sodium hyaluronate (molecular weight ca. 1.5 million) was dissolved in 2 L distilled water, concentrated hydrochloric acid was added to adjust the solution pH to about 0.5, then the solution was degraded for 24 hours in a swing incubator at 37° C., a speed of 150 rpm. Low-molecular-weight hyaluronic acid ($M_w$ 0.246 million, $M_n$ 0.12 million) was obtained after purification by dialysising and lyophilizing.

The low-molecular-weight hyaluronic acid (20 g) was dissolved in 2 L distilled water, 23.8 g dithiobis(propanoic hydrazide) (prepared in accordance with the method disclosed by Shu et al in Biomacromolecules, 3, 1304, 2002), was added into the above solution and stirred to dissolve. Then 1 mol/L hydrochloric acid was used to adjust the solution pH to 4.75, 19.2 g 1-ethyl-3-(3-dimethylamine propyl) carbodiimide hydrochloride (Aldrich, USA) was added under electromagnetic stirring. 0.1 mol/L hydrochloric acid was continuously added in the above solution to keep the pH value of the solution at 4.75. 1.0 mol/L sodium hydroxide solution was added till pH=7.0 to terminate the reaction, then 100 g dithiothreitol (Diagnostic Chemical Limited, USA) and appropriate amount of 1.0 mol/L sodium hydroxide solution were added under stirring. The solution pH was adjusted to 8.5, and conducted reaction at room temperature under electromagnetic stirring for 24 hours. After that, 1 mol/L hydrochloric acid was added into the above solution till the pH value was about 3.5. The above solution was filled into dialysis tube (molecular weight cut-off 3,500, Sigma, USA), and dialysized against large amount of 0.0003 mol/L hydrochloric acid and 0.1 mol/L sodium chloride solution for 5 days with the change of dialysis solution every 8 hours; and then further dialysized against large amount 0.0003 mol/L hydrochloric acid solution with the change of dialysis solution every 8 hours. Finally the solution in the dialysis tube was collected and lyophilized to give white flocc solid (HA-DTPH).

The above HA-DTPH was dissolved in the distilled water to give 1.0~2.5% w/v solution and the solution pH was adjusted to 2.0~7.0, and the solution was sterilized by filtration and stored under frozen for use (usually below minus 20° C.). Or during the above preparation process, the solution after purification by dialysising was concentrated and dehydrated through dialysis column to appropriate concentration (usually 1.0~2.5% w/v), and the pH value of solution was adjusted to 2.0~7.0, sterilized by filtration stored under frozen for use (usually below minus 20° C.).

The substitution degree of side-chain thiol of HA-DTPH was 42/100 disaccharide repeated units by $^1$H-NMR detection (with $D_2O$ as solvent); and the molecular weight and its polydispersity (determined by GPC) were: $M_w$ 0.136 million and $M_n$ 61 thousands.

Example 2

Preparation of Biocompatible Thiol-Reactive Crosslinking Agent

Polyethylene glycol diacrylate, polyethylene glycol di(methyl)acrylate, polyethylene glycol diacrylamide and polyethylene glycol di(methyl)acrylamide were prepared using corresponding polyethylene glycol (molecular weight 3400 or 10000, Sigma-Aldrich, USA) and polyethylene glycol diamine (molecular weight 3400, Nektar Therapeutics, USA), multi-arm (four-arm and eight-arm) polyethylene glycol diacrylate and polyethylene glycol di(methyl)acrylate were prepared using corresponding multi-arm polyethylene glycol (molecular weight 10,000). The general process of the preparation is that, polyethylene glycol or polyethylene glycol diamine reacts with acryloyl chloride or methacryloyl chloride under the effect of triethylamine, and the products can be obtained after purification. Shu et al., Biomaterials, 25, 1339, 2004 shows the detailed procedures.

If halogenated acyl chloride (e.g. iodo-propionyl chloride and bromo-propionyl chloride, etc.) was used instead of the corresponding acryloyl chloride, the same process as described above can be used to prepare the thiol-reactive cross-linking agents e.g. polyethylene glycol diiodo propionate, polyethylene glycol dibromo propionate, polyethylene glycol dichloro propionate, polyethylene glycol diiodo propionamide, polyethylene glycol dibromo propionamide, polyethylene glycol dichloro propionamide etc.

Example 3

Preparation of Biocompatible Rapid-Gelating Hydrogel

The HA-DTPH solution (2.0% w/v, pH=5.0) prepared by Example 1 was defrosted at room temperature for use. Polyethylene glycol diacrylate (molecular weight 3400, Nektar Therapeutics, USA) was dissolved in 0.3 mol/L sodium phosphate/sodium carbonate buffer solution to give a 2.0% w/v solution (pH=9.6), and sterilized by filtration for use. Under electromagnetic stirring, the above one solution (5 ml) was added into another solution (5 ml) quickly, continued stirring for 3 seconds and then stopped stirring, the pH value of reactive mixture was about 9.4, and the mixture solution lost its fluidity to form gel after about 17 seconds.

Example 4

Preparation of Biocompatible Rapid-Gelating Hydrogel

The HA-DTPH solution (1.5% w/v, pH=6.0) prepared by Example 1 was defrosted at room temperature for use. Polyethylene glycol diacrylate (molecular weight 3400, Nektar Therapeutics, USA) was dissolved in 0.15 mol/L sodium phosphate/sodium carbonate buffer solution to give a 1.5% w/v solution (pH=9.6), and sterilized by filtration for use. Under electromagnetic stirring, the above one solution (5 ml) was added into another solution (5 ml) quickly, continued stirring for 3 seconds and then stopped stirring, the pH value of reactive mixture was about 9.3, and the mixture solution lost its fluidity to form gel after about 27 seconds.

Example 5

Preparation of Biocompatible Rapid-Gelating Hydrogel

The HA-DTPH solution (1.5% w/v, pH=6.0) prepared by Example 1 was defrosted at room temperature for use. Polyethylene glycol diacrylate (molecular weight 3400, Nektar Therapeutics, USA) was dissolved in 0.3 mol/L boric acid/sodium hydroxide buffer solution to give a 1.5% w/v solution (pH=11), and sterilized by filtration for use. Under electromagnetic stirring, the above one solution (5 ml) was added into another solution (5 ml) quickly, continued stirring for 3 seconds and then stopped stirring, the pH value of reactive mixture was higher than 10.5, and the mixture solution lost its fluidity to form gel in less than 10 seconds.

Example 6

Preparation of Biocompatible Rapid-Gelating Hydrogel

The HA-DTPH solution (1.0% w/v, pH=5.0) prepared by Example 1 was defrosted at room temperature for use. Polyethylene glycol divinyl sulfone (molecular weight 3400, Nektar Therapeutics, USA) was dissolved in 0.3 mol/L sodium phosphate/sodium carbonate buffer to give a 1.0% w/v solution (pH=9.6), and sterilized by filtration for use. Under electromagnetic stirring, the above one solution (5 ml) was added into another solution (5 ml) quickly, continued stirring for 3 seconds and then stopped stirring, the pH value of reactive mixture was about 9.3, and the mixture solution lost its fluidity to form gel after about 48 seconds.

Example 7

Preparation of Biocompatible Rapid-Gelating Hydrogel

The HA-DTPH solution (2.5% w/v, pH=5.0) prepared by Example 1 was defrosted at room temperature for use. Polyethylene glycol divinyl sulfone (molecular weight 3400, Nektar Therapeutics, USA) was dissolved in 0.3 mol/L sodium phosphate/sodium carbonate buffer solution to give a 2.0% w/v solution (pH=7.4), and sterilized by filtration for use. Under electromagnetic stirring, the above one solution (5 ml) was added into another solution (5 ml) quickly, continued stirring for 3 seconds and then stopped stirring, the pH value of reactive mixture was about 7.2, and the mixture solution lost its fluidity to form gel after about 5 minutes.

Example 8

Preparation of Biocompatible Rapid-Gelating Hydrogel

The HA-DTPH solution (2.0% w/v, pH=6.0) prepared by Example 1 was defrosted at room temperature for use. Polyethylene glycol dibromo propionate (molecular weight 3400, Nektar Therapeutics, USA) was dissolved in 0.15 mol/L sodium phosphate buffer solution to give a 2.0% w/v solution (pH=7.4), and sterilized by filtration for use. Under electromagnetic stirring, the above one solution (5 ml) was added into another solution (5 ml) quickly, continued stirring for 3 seconds and then stopped stirring, the pH value of reactive mixture was about 7.2, and the mixture solution lost its fluidity to form gel after about 5 minutes.

Example 9

Preparation of Biocompatible Rapid-Gelating Hydrogel

The HA-DTPH solution (2.0% w/v, pH=7.0) prepared by Example 1 was defrosted at room temperature for use. Polyethylene glycol divinyl sulfone (molecular weight 3400, Nektar Therapeutics, USA) was dissolved in 0.15 mol/L sodium phosphate buffer solution to give a 2.0% w/v solution (pH=8.2), and sterilized after filtration for use. Under electromagnetic stirring, the above one solution (5 ml) was added into another solution (5 ml) quickly, continued stirring for 3 seconds and then stopped stirring, the pH value of reactive mixture was about 8.0, and the mixture solution lost its fluidity to form gel after about 2 minutes.

Example 10

Preparation of Biocompatible Rapid-Gelating Hydrogel

The HA-DTPH solution (2.0% w/v, pH=5.0) prepared by Example 1 was defrosted at room temperature for use. Polyethylene glycol diacrylate (molecular weight 3400, Nektar Therapeutics, USA) was dissolved in 0.0005 mol/L sodium phosphate buffer solution to give a 8.0% w/v solution (pH=6.0), and sterilized by filtration for use. Under electromagnetic stirring, the above polyethylene glycol diacrylate solution (1 ml) was added into HA-DTPH solution (4 ml) quickly, the pH value of reactive mixture was about 5.4, and then 5 ml 0.3 mol/l sodium phosphate/sodium carbonate buffer solution (pH 9.6) was added, continued stirring for 3 seconds and then stopped stirring, the pH value of reactive mixture was about 9.3, and the mixture solution lost its fluidity to form gel after about 21 seconds.

Example 11

Preparation of Biocompatible Rapid-Gelating Hydrogel

The HA-DTPH solution (2.0% w/v, pH=3.0) prepared by Example 1 was defrosted at room temperature for use. Polyethylene glycol diacrylate (molecular weight 3400, Nektar Therapeutics, USA) was dissolved in 0.001 mol/L hydrochloric acid to give an 8.0% w/v solution, and sterilized after filtration for use. Under electromagnetic stirring, the above polyethylene glycol diacrylate solution (1 ml) was added into HA-DTPH solution (4 ml) quickly, the pH value of reactive mixture was about 3.0, and then under electromagnetic stirring sufficient 0.1 mol/l sodium hydroxide solution was added to adjust solution pH to 7.2, and the mixture solution lost its fluidity to form gel after about 6 minutes.

Example 12

Preparation of Biocompatible Rapid-Gelating Hydrogel

The HA-DTPH solution (2.0% w/v, pH=3.0) prepared by Example 1 was defrosted at room temperature for use. Polyethylene glycol diacrylate (molecular weight 3400, Nektar Therapeutics, USA) was dissolved in 0.001 mol/L hydrochloric acid to give an 8.0% w/v solution, and sterilized by filtration for use. Under electromagnetic stirring, the above polyethylene glycol diacrylate solution (1 ml) was added into HA-DTPH solution (4 ml) quickly, the pH value of reactive mixture was about 3.0, and then under electromagnetic stirring sufficient 0.1 mol/l sodium hydroxide solution was added to adjust solution pH to 8.0, and the mixture solution lost its fluidity to form gel after about 2 minutes.

Example 13

Preparation of Biocompatible Rapid Gelating Hydrogel

The HA-DTPH solution (2.0% w/v, pH=4.0) prepared by Example 1 was defrosted at room temperature for use. Polyethylene glycol diacrylate (molecular weight 3400, Nektar Therapeutics, USA) was dissolved in 0.0001 mol/L hydrochloric acid to give an 8.0% w/v solution, and sterilized by filtration for use. Under electromagnetic stirring, the above polyethylene glycol diacrylate solution (1 ml) was added into HA-DTPH solution (4 ml) quickly, the pH value of reactive mixture was about 4.0, and then under electromagnetic stirring sufficient 0.1 mol/l sodium hydroxide solution was added to adjust solution pH to 11.3, and the mixture solution lost its fluidity to form gel after about 39 seconds.

Example 14

Preparation of Biocompatible Rapid Gelating Hydrogel

The HA-DTPH solution (2.0% w/v, pH=5.0) prepared by Example 1 was defrosted at room temperature for use. 75 mg polyethylene glycol diacrylate (molecular weight 3400, Nektar Therapeutics, USA) was added into above solution, shaked with hands to obtain the mixed solution, Under electromagnetic stirring, 5 ml 0.3 mol/l sodium phosphate/sodium carbonate buffer solution (pH 9.6) (1 ml) was added quickly, continued stirring for 3 seconds and then stopped stirring, the pH value of reactive mixture was about 9.3, and the mixture solution lost its fluidity to form gel after about 37 seconds.

Example 15

Preparation of Rapid-Gelating Hydrogel Spray

The HA-DTPH solution (2.0% w/v, pH=5.0) prepared by Example 1 was defrosted at room temperature for use. Polyethylene glycol diacrylate (molecular weight 3400, Nektar Therapeutics, USA) was dissolved in 0.3 mol/L sodium phosphate/sodium carbonate buffer solution to give a 1.5% w/v solution (pH=9.6), and sterilized by filtration for use. 5 ml of each above two solutions was filled into the FibriJet gas assisted atomization applicator kit (Type: SA-6110, Micromedics Inc, USA), the solutions were then atomized under nitrogen gas of 1.5 atmospheric pressure and sprayed onto the vertical glass plate where the mixture solution nearly did not flow, and formed an uniform gel film on the surface of glass plate rapidly.

Example 16

Preparation of Rapid Gelating Hydrogel Spray

The HA-DTPH solution (1.5% w/v, pH=4.0) prepared by Example 1 was defrosted at room temperature for use. 75 mg polyethylene glycol diacrylate (molecular weight 3400, Nektar Therapeutics, USA) was dissolved into above 5 ml solution, and shaked with hands to obtain mixed solution. 5 ml of above mixed solutions and 0.3 mol/L carbonate buffer solution (pH=10.5) were filled into the FibriJet gas assisted atomization applicator kit (Type: SA-6110, Micromedics Inc, USA), respectively, the solutions were then atomized under nitrogen gas of 3 atmospheric pressure and sprayed onto the vertical glass plate where the mixture solution nearly did not flow, and formed an uniform gel film on the surface of glass plate rapidly.

Example 17

Preparation of Rapid-Gelating Hydrogel Spray

The HA-DTPH solution (1.5% w/v, pH=5.0) prepared by Example 1 was defrosted at room temperature for use. Polyethylene glycol divinyl sulfone (molecular weight 3400, Nektar Therapeutics, USA) was dissolved in 0.3 mol/L sodium phosphate/sodium carbonate buffer solution to give a 1.5% w/v solution (pH=10.0), and sterilized by filtration for use. 5 ml of each above two solutions was filled into the FibriJet gas assisted atomization applicator kit (Type: SA-6110, Micromedics Inc, USA), the solutions were then atomized under nitrogen gas of 1.5 atmospheric pressure and sprayed onto the vertical glass plate where the mixture solution nearly did not flow, and formed an uniform gel film on the surface of glass plate rapidly.

Example 18

Preparation of Rapid-Gelating Hydrogel Spray

The HA-DTPH solution (1.5% w/v, pH=5.0) prepared by Example 1 was defrosted at room temperature for use. Polyethylene glycol di(methyl)acrylate (molecular weight 3400, Nektar Therapeutics, USA) was dissolved in 0.3 mol/L disodium hydrogen phosphate/sodium hydroxide buffer solution to give a 1.5% w/v solution (pH=12.0), and sterilized by filtration for use. 5 ml of each above two solutions was filled into the FibriJet gas assisted atomization applicator kit (Type: SA-6110, Micromedics Inc, USA), the solutions were then atomized under nitrogen gas of 5 atmospheric pressure and sprayed onto the vertical glass plate where the mixture solution nearly did not flow, and formed an uniform gel film on the surface of glass plate rapidly.

Example 19

Preparation of Rapid-Gelating Hydrogel Spray

The HA-DTPH solution (2.5% w/v, pH=5.0) prepared by Example 1 was defrosted at room temperature for use. Polyethylene glycol diacrylamide (molecular weight 3400) prepared by Example 2 was dissolved in 0.3 mol/L disodium hydrogen phosphate/sodium hydroxide buffer solution to give a 2.5% w/v solution (pH=12.0), and sterilized by filtration for use. 5 ml of each above two solutions was filled into the FibriJet gas assisted atomization applicator kit (Type: SA-6110, Micromedics Inc, USA), the solutions were then atomized under nitrogen gas of 5 atmospheric pressure and sprayed onto the vertical glass plate where the mixture solution nearly did not flow, and formed an uniform gel film on the surface of glass plate rapidly.

Example 20

Preparation of Disuccinate Diacyl Cystamine Dihydrazide (Abbr. DSCDH)

Cystamine dihydrochloride 100 g (Aldrich, USA) was dissolved into 1500 ml distilled water to give a clear and transparent solution. NaOH (4 mol/L) was added into the above solution until pH 10. Then under magnetic stirring, succinic anhydride 133 g (Aldrich, USA) was added, and NaOH (4 mol/L) was simultaneously added to keep solution pH at 7~10. After 2 h reaction at room temperature, HCl (6 mol/L) was added into the solution, the white precipitated product was collected by filtration, washed twice with 2000 ml distilled water, and then dried under reduced pressure to give white solid product (disuccinate diacyl cystamine diacid, abbr. DSC) of approximately 150 g (yield is higher than 90%).

In a 250 ml three-neck round-bottom flask, DSC 100 g, anhydrous alcohol 1200 ml and concentrated sulfuric acid 100 drops were added. After refluxed for 2 hours under nitrogen protection, the solution was concentrated under reduced pressure to a volume less than 200 ml. Then the remained solution was transferred into a 2500 ml tap funnel, and ethyl acetate 600 ml was added. Then the organic phase was washed with 500 ml water three times, the aqueous phase was abandoned, and the organic phase was distilled under reduced pressure to give white lardaceous solid product (disuccinate diacyl cystamine diethyl ester, DSCDE) of approximately 93 g (yield is higher than 80%).

In a 150 ml beaker, DSCDE 10 g and alcohol 80 ml were added and dissolved under stirring, and then hydrazine hydrate 10 ml (Aldrich, USA) was added. After overnight reaction, the white precipitated product was collected by filtration, and rinsed 4 times with 40 ml alcohol. The organic solvent was evaporated at room temperature in a fume hood, and then the product was dried under reduced pressure to give white solid DSCDH of about 8 g (yield is higher than 75%).

Example 21

Preparation of Thiolated Hyaluronic Acid (Ha-DSCDH)

10 g Sodium hyaluronate (molecular weight ca. 0.2-1.15 million, Novamatrix FMC BIOMACROMOLECULE, USA) was dissolved into 2 L distilled water to give a clear and transparent solution. 9.5 g DSCDH prepared by Example 20 was added into the above solution and stirred to dissolve. Then 1 mol/L hydrochloric acid was used to adjust the solution pH to 4.75, 2.88 g 1-ethyl-3-(3-dimethylamine propyl) carbodiimide hydrochloride (Aldrich, USA) was added under electromagnetic stirring. 0.1 mol/L hydrochloric acid was continuously added in the above solution to keep the pH value at 4.75. The viscosity of the solution continuously increased, and a gel formed after about 10 minutes. After the gel formed, it was kept still at room temperature for 2 hours. Then 100 g dithiothreitol (Diagnostic Chemical Limited, USA) and small amount of 1.0 mol/L sodium hydroxide solution were added under stirring. The gel gradually dissolved, at the same time, the solution pH was kept at 8.5 by adding 1.0 mol/L sodium hydroxide solution. After the gel was completely dissolved, the reaction was conducted at room temperature under electromagnetic stirring for 24 hours. After that, hydrochloric acid (6 mol/L) was added into the above solution till the pH value was about 3.0. The above solution was filled into dialysis tube (molecular weight cut-off 3,500, Sigma, USA), and dialysized using 20 L 0.001 mol/L hydrochloric acid and 0.3 mol/L sodium chloride solution for 5 days with the change of dialysis solution every 8 hours; and then further dialysized using 20 L 0.001 mol/L hydrochloric acid solution for three days with the change of dialysis solution every 8 hours. Finally, the solution in the dialysis tube dehydrated and concentrated in a dialysis column to certain concentration (0.8~1.5% w/v), and the solution pH was adjusted to 3.0~8.5. After sterilized by filtration, the solution was stored under frozen for use (usually below minus 20° C.).

The improved Ellman method, reported by Shu et al in Biomacromolecules, 3, 1304, 2002, was used to detect the active thiol content in HA-DSCDH: 39.1 thiol/100 hyaluronic acid disaccharide repeated units, which was mainly in accordance with the $^1$H-NMR detection result.

Example 22

Preparation of Rapid-Gelating Hydrogel

The HA-DSCDH solution (0.8% w/v, pH=4.0) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into 0.3 mol/L sodium phosphate/sodium carbonate buffer solution to give a 1.0% w/v solution (pH=9.6), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 9.3, and the mixture solution lost its fluidity to gel after about 47 seconds.

Example 23

Preparation of Rapid-Gelating Hydrogel

The HA-DSCDH solution (0.5% w/v, pH=7.0) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into 0.3 mol/L sodium phosphate/sodium hydroxide buffer solution to give a 0.8% w/v solution (pH=12.0), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 12.0, and the mixture solution lost its fluidity to form gel after about 17 seconds.

Example 24

Preparation of Rapid-Gelating Hydrogel

The HA-DSCDH solution (1.2% w/v, pH=3.5) prepared by Example 21 was defrosted at room temperature for use. Four-arm polyethylene glycol diacrylate (mean 3.6 acrylate functional groups/four-arm polyethylene glycol, molecular weight 10,000) prepared in Example 2 was dissolved into 0.15 mol/L sodium phosphate/sodium carbonate buffer solution to give a 1.2% w/v solution (pH=9.6), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 9.2, and the mixture solution lost its fluidity to form gel after about 29 seconds.

Example 25

Preparation of Rapid-Gelating Hydrogel

The HA-DSCDH solution (1.2% w/v, pH=7.0) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into 0.3 mol/L carbonate buffer solution to give a 0.5% w/v solution (pH=8.5), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 8.5, and the mixture solution lost its fluidity to form gel after about 3 minutes.

Example 26

Preparation of Rapid-Gelating Hydrogel

Temperature the HA-DSCDH solution (1.2% w/v, pH=7.0) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into 0.30 mol/L phosphate buffer solution to give a 1.2% w/v solution (pH=8.5), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 8.0, and the mixture solution lost its fluidity to form gel after about 4 minutes.

Example 27

Preparation of Rapid-Gelating Hydrogel

The HA-DSCDH solution (1.2% w/v, pH=2.5) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into 0.3 mol/L phosphate/carbonate buffer solution to give a 1.0% w/v solution (pH=9.6), and sterilized by filtration for use. Under electromagnetic stirring, the HA-DSCDH solution (5 ml) was added into four-arm polyethylene glycol diacrylate solution (5 ml) quickly, continued stirring for 3 seconds and then stopped stirring, the pH value of reactive mixture was about 9.2, and the mixture solution lost its fluidity to form gel after about 29 seconds.

Example 28

Preparation of Rapid-Gelating Hydrogel

The HA-DSCDH solution (1.2% w/v, pH=2.5) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into hydrochloric acid solution (pH=2.5) to give a 1.0% w/v solution, and sterilized by filtration for use. Under electromagnetic stirring, the HA-DSCDH solution (5 ml) was added into four-arm polyethylene glycol diacrylate solution (5 ml) quickly, and the pH value of the mixed solution was about 2.5. Under electromagnetic stirring, sufficient 0.1 mol/L sodium hydroxide solution was added to adjust the pH value of reactive mixture to 10.5, and the mixture solution lost its fluidity to form gel (less than 10 seconds).

Example 29

Preparation of Rapid-Gelating Hydrogel

The HA-DSCDH solution (1.2% w/v, pH=3.5) prepared by Example 21 was defrosted at room temperature for use. Four-arm polyethylene glycol diacrylate (average 3.6 acrylate functional groups/four-arm polyethylene glycol, molecular weight 10,000) prepared in Example 2 was dissolved into hydrochloric acid solution (pH=3.5) to give a 1.0% w/v solution, and sterilized by filtration for use. Under electromagnetic stirring, the HA-DSCDH solution (5 ml) was added into four-arm polyethylene glycol diacrylate solution (5 ml) quickly, and the pH value of the mixed solution was about 3.5. Under electromagnetic stirring, appropriate amount of 0.3 mol/L sodium hydroxide solution was added to adjust the pH value of reactive mixture to 12, and the mixture solution lost its fluidity to form gel within several seconds.

Example 30

Preparation of Rapid-Gelating Hydrogel Spray

The HA-DSCDH solution (1.0% w/v, pH=8.0) prepared by Example 21 was defrosted at room temperature for use. Four-arm polyethylene glycol acrylate (mean 3.6 acrylate functional groups/four-arm polyethylene glycol, molecular weight 10,000) prepared in Example 2 was dissolved into 0.3 mol/L carbonate buffer solution to give a 1.0% w/v solution (pH=10.5). 5 ml of HA-DTPH solution and four-arm polyethylene glycol acrylate solution was respectively filled into the FibriJet gas assisted atomization applicator kit (Type: SA-6110, Micromedics Inc, USA), respectively, the solutions were then atomized under nitrogen gas of 3 atmospheric pressure and sprayed onto the vertical glass plate where the mixture solution nearly did not flow, and formed an uniform gel film on the surface of glass plate rapidly.

Example 31

Synthesis and Characterization of Thiolated Chondroitin Sulphate (CS-DSCDH)

1 g chondroitin sulfate (C-type, from shark cartilage, Sigma, USA) was dissolved into 100 ml distilled water to give a clear and transparent solution. 0.704 g DSCDH prepared by Example 20 was added into the above solution and stirred to dissolve. Then 1 mol/L hydrochloric acid was used to adjust the solution pH to 4.75, 0.192 g 1-ethyl-3-(3-dimethylamine propyl) carbodiimide hydrochloride (Aldrich, USA) was added under electromagnetic stirring. Sufficient 0.1 mol/L hydrochloric acid was continuously added in the above solution to keep the pH value of the solution at 4.75. The reaction was conducted at room temperature for 2 hours. Then 10 g dithiothreitol (Diagnostic Chemical Limited, USA) and small amount of 1.0 mol/L sodium hydroxide solution were added under stirring. The gel gradually dissolved, at the same time, the solution pH was kept at 8.5 by adding 1.0 mol/L sodium hydroxide solution. After the gel was completely dissolved, the reaction was conducted at room temperature under electromagnetic stirring for 24 hours. After that, hydrochloric acid (6 mol/L) was added into the above solution till the pH value was about 3.0. The above solution was filled into dialysis tube (molecular weight cut-off 3,500, Sigma, USA), and dialysized against 10 L 0.001 mol/L hydrochloric acid and 0.3 mol/L sodium chloride solution for 5 days with the change of dialysis solution every 8 hours; and then further dialysized against 10 L 0.001 mol/L hydrochloric acid solution for three days with the change of dialysis solution every 8 hours. Finally, the solution in the dialysis tube dehydrated and concentrated in a dialysis column to certain concentration (3.0~6.0% w/v), and the solution pH was adjusted to 3.0~8.5. After sterilized by filtration, the solution was stored under frozen for use (usually below minus 20° C.).

The side-chain substitution degree of synthetic CS-DSCDH was calculated to be 47% according to the area of absorption peak using the characteristic methyl absorption peak of acetyl group in chondroitin sulfate as internal standard, The molecular weight and its distribution were determined by GPC: Mw 38 thousands, Mn17 thousands and polydispersity index 2.23.

The improved Ellman method, reported by Shu et al in Biomacromolecules, 3, 1304, 2002, was used to detect the active thiol content in Cs-DSCDH: 44.2 thiol/100 chondroitin sulfate disaccharide repeated units.

Example 32

Preparation of Rapid-Gelating Hydrogel

The CS-DSCDH solution (6.0% w/v, pH=5.0) prepared by Example 31 at room temperature was ready for use. The four-arm polyethylene glycol acrylate (mean 3.6 acrylate functional groups/four-arm polyethylene glycol, molecular weight 10,000) prepared in Example 2 was dissolved into 0.3 mol/l carbonate buffer solution to give a 6.0% w/v solution (pH=10.5), and sterilized by filtration for use. Under electromagnetic stirring, the above one solution (5 ml) was added into another solution (5 ml) quickly, continued stirring for 3 seconds and then stopped stirring, and the mixture solution lost its fluidity to form gel within 10 seconds.

Example 33

Preparation of Rapid-Gelating Hydrogel

The CS-DSCDH solution (6.0% w/v, pH=5.0) prepared by Example 31 at room temperature was ready for use. The four-arm polyethylene glycol acrylate (mean 3.6 acrylate functional groups/four-arm polyethylene glycol, molecular weight 10,000) prepared in Example 2 was dissolved into 0.005 mol/L phosphate buffer solution to give a 6.0% w/v solution (pH=7.0), and sterilized by filtration for use. Under electromagnetic stirring, the above one solution (5 ml) was added into another solution (5 ml) quickly, and the pH value of reactive mixture was 7.0. Under electromagnetic stirring, sufficient 0.3 mol/L sodium hydroxide solution was added to adjust the pH value of reactive mixture to 10.5, and the reactive mixed solution immediately lost its fluidity to form gel (less than 10 seconds).

Example 34

Preparation of Rapid-Gelating Hydrogel

The CS-DSCDH solution (3.0% w/v, pH=4.0) prepared by Example 31 at room temperature was ready for use. The four-arm polyethylene glycol acrylate (average 3.6 acrylate functional groups/four-arm polyethylene glycol, molecular weight 10,000) prepared in Example 2 was dissolved into 0.3 mol/l boric acid/sodium hydroxide buffer solution to give a 3.0% w/v solution (pH=11), and sterilized by filtration for use. Under electromagnetic stirring, the pH value of CS-DSCDH was adjusted to 8.5 with alkali, and then four-arm polyethylene glycol acrylate solution (5 ml) was added quickly. The pH value of reactive mixture was about 11.0, and the reactive mixture immediately lost its fluidity to form gel.

Example 35

Preparation of Rapid-Gelating Hydrogel Spray

The CS-DSCDH solution (4.0% w/v, pH=8.0) prepared by Example 31 at room temperature was ready for use. The four-arm polyethylene glycol acrylate (average 3.6 acrylate functional groups/four-arm polyethylene glycol, molecular weight 10,000) prepared in Example 2 was dissolved into 0.3 mol/L carbonate buffer solution to give a 4.0% w/v solution (pH=10.5), and sterilized by filtering for use. 5 ml each of above solution was respectively filled into the FibriJet gas assisted atomization applicator kit (Type: SA-6110, Micromedics Inc, USA) respectively, the solutions were then atomized under nitrogen gas of 2 atmospheric pressure and sprayed onto the vertical glass plate where the mixture solution nearly did not flow, and formed an uniform gel film on the surface of glass plate rapidly.

Example 36

Preparation of Thiolated Gelatin (1) Succinyl carboxylation modification of gelatin 1 g gelatin (B-type, from the pigskin, Sigma, USA) was dissolved into 100 ml distilled water (about 30° C.) to give clear and transparent solution. The solution pH was adjusted to about 9.5 by adding 1.0 mol/L sodium hydroxide solution, and then 0.05 g succinate anhydride (analytical pure) was added under electromagnetic stirring, and appropriate amount of 1.0 mol/L sodium hydroxide was continuously added to keep the pH value of the solution at weakly alkaline (usually at 8.0~9.5). The reaction was conducted at 30° C. under stirring for 1 hour. Since then, the above solution was filled into a dialysis tube (molecular weight cut-off 3,500, Sigma, USA) and dialyzed against distilled water with the change of dialysis solution every 8 hours, till there was no the eluting peak of small molecule impurity detected by GPC (with pure water as the mobile phase, detected according to the absorption at UV 210 nm). Finally, the solution in dialysis tube was collected, lyophilized to get white flocc solid (succinyl carboxylate gelatin) about 0.7 g.

(2) Thiol Modification of Succinyl Carboxylate Gelatin 0.5 g above succinyl carboxylate gelatin was dissolved into 50 ml distilled water (about 30° C.), 1.2 g dithiobis(propanoic hydrazide) (prepared according to the method disclosed by Shu et al in Biomacromolecules, 3, 1304, 2002) was added in the above solution and dissolved under stirring. Then the solution pH was adjusted to 4.75 by adding 0.1 mol/L hydrochloric acid, and 0.75 g 1-ethyl-3-(3-dimethylamine propyl) carbodiimide hydrochloride (Aldrich, USA) was added with electromagnetic stirring. Appropriate amount of 0.1 mol/L hydrochloric acid was continuously added in the above solution added to keep the pH value of the solution at 4.75. The reaction was conducted at room temperature under electromagnetic stirring for 2 hours, then 5 g dithiothreitol (Diagnostic Chemical Limited, USA) and 1.0 mol/L sodium hydroxide solution were added with stirring to adjust the pH value of the solution to 8.5. After the reaction was conducted for 24 hours at room temperature under electromagnetic stirring, hydrochloric acid (6 mol/l) was added in the above solution till its pH value was about 3.0. The above solution was then filled into a dialysis tube (molecular weight cut-off 3,500, Sigma, USA), and dialysized using 10 L 0.001 mol/L hydrochloric acid and 0.3 mol/L sodium chloride solution for 5 days with the change of dialysis solution every 8 hours; and then further dialysized using 10 L 0.001 mol/L hydrochloric acid solution with change of dialysis solution every 8 hours, till there was no the eluting peak of small molecule impurity detected by GPC. Finally the solution in dialysis tube was collected, lyophilized to give white flocc solid about 0.33 g. The above products was dissolved in distilled water to give 3.0~5.0% w/v solution, and the solution pH was adjusted to 2.0~7.0, after sterilized by filtering, the solution was stored under frozen for use (usually below minus 20° C.).

The side-chain amino groups of succinyl carboxylate gelatin was determined by 2,4,6-trinitro-benzene-sulfonic acid (TNBS), wherein about 45% amino groups were modified with succinyl carboxylation.

The active thiol content in gelation multi-modification derivative of succinyl carboxylation and thiolation was determined by the improved Ellman method reported by Shu et al. in Biomacromolecules, 3, 1304, 2002, and thiolation degree of gelatin multi-modification derivative: 0.87 mmol thiol/grams.

Example 37

Preparation of Rapid-Gelating Hydrogel

The thiolated gelatin solution (5.0% w/v, pH=7.0) prepared by Example 36 was ready for use. The four-arm polyethylene glycol acrylate (mean 3.6 acrylate functional groups/four-arm polyethylene glycol, molecular weight 10,000) prepared in Example 2 was dissolved into 0.3 mol/L boric acid/sodium hydroxide buffer solution to get a 4.0% w/v solution (pH=11.0). Under electromagnetic stirring, one above solution (5 ml) was added into another solution (5 ml), continued stirring for 3 seconds and then stopped stirring, and the reactive mixture solution lost its fluidity to form gel after about 29 seconds.

Example 38

Application of Rapid-Gelating Hydrogel Spray in Prevention and Treatment of Postoperative Adhesion The rat cecum model reported by Dunn et al (Dunn et al, Fertility & Sterility, 75, 411, 2001) was adopted. Its process was briefly stated as follows: the lateral surfaces and ventral surfaces of 12 rats' cecum were scraped using sterile gauze till the surfaces bleeded. The corresponding abdominal walls were scraped out $1 \times 2$ cm$^2$ areas till the surfaces bleeded. The rapid-gelating hydrogel spray prepared by Example 15 was sprayed on the wound surfaces and also the whole abdominal cavity of 6 rats, and finally the wounds of rat body surfaces were sutured. Two weeks later the rats were killed, and dissected them to observe the adhesive conditions. The amount of hydrogel used for each rat was about 1.5 ml, and the left untreated 6 rats were used as the control group. Two weeks later, the result of the anatomy for rats indicated that, the rats in control groups all showed compact adhesion, while there was no any adhesion in treatment group.

Industrial Practicability

The beneficial effects of the preparation method for biocompatible rapid-gelating hydrogel in this invention include many advantages e.g. good biocompatibility, no byproduct or not generating the byproduct with toxic and side effects, good stability of each adopted component, less amount used, low cost, easy to use, easy to realize rapid-gelation, easy to realize the preparation of rapid-gelating hydrogel spray, and suitable for various medical purposes etc. Compared with the method disclosed by Wallace et al (Wallace et al, U.S. Pat. No. 6,624, 245), this invention have many advantages e.g. no byproduct or not generating the byproduct with toxic and side effects, better biocompatibility, more stable crosslinking chemical bonds, better stability of adopted active components, less amount of active components used and lower cost etc.

The beneficial effects of the preparation method for biocompatible rapid-gelating hydrogel of this invention also include suitable for industrial large-scale production. As aforementioned, the biocompatible thiolated macromolecule of component A adopted by this invention is very unstable under relatively strong alkaline conditions. Therefore, when the biocompatible thiolated macromolecule solution adopted by this invention is relatively strong alkaline, it may lose its activity and not suitable for industrial large-scale production. While in this invention, the pH value of component A containing biocompatible thiolated macromolecule is less than 8.5, and it is usually weakly acidic, therefore it has good stability, and many procedures (such as sterilizing, filling, packaging and storage etc) can be conveniently finished during the industrial large-scale production. In addition, after the purification process during the preparation of biocompatible thiolated macromolecule, the component A adopted by the invention does not need to be lyophilized, and it can enter the next procedure directly or after being concentrated or diluted to a certain concentration, which avoids the lyophilizing procedure which is both time-consuming and labor-consuming.

The preparation method for biocompatible rapid-gelating hydrogel spray of this invention has the advantages of aforementioned preparation method for rapid-gelating hydrogel; at the same time, it has the advantage of simplicity and convenience, convenient for use, suitable for various medical uses e.g. treatment of adhesion complication etc. In addition, the preparation method for the gas assisted atomization spray also adopts mixing under atomization condition, which may not block the applicator tip and can be used multiple times.

The invention claimed is:

1. A preparation method for biocompatible rapid-gelating hydrogel, wherein the method comprises:
   mixing a component A and a component B to form a reactive mixture,
      wherein the component A is a solution containing biocompatible thiolated macromolecule derivatives, and the component B is a solution containing a biocompatible thiol-reactive crosslinking agent,
      wherein the biocompatible thiolated macromolecule derivatives are prepared through thiolation of biocompatible macromolecules,
      wherein the concentration of the biocompatible thiolated macromolecule derivatives in component A is less than 8% w/v,
      wherein a sum of a concentration of the biocompatible thiolated macromolecule derivatives and a concentration of the biocompatible thiol-reactive crosslinking agent in the reactive mixture is less than 6% w/v, and
      wherein a pH value of the component A ranges from 3.5-6,
      wherein a pH value of the component B is more than 8.5; and
   crosslinking thiol groups of the component A with thiol-reactive functional groups of the component B to form a hydrogel.

2. The preparation method for biocompatible rapid-gelating hydrogel according to claim 1, wherein the biocompatible thiolated macromolecule derivative contains at least 3 thiols, with a molecular weight of 1,000-10,000,000.

3. The preparation method for biocompatible rapid-gelating hydrogel according to claim 1, wherein the biocompatible macromolecule includes polysaccharides, their salt forms and chemical modified forms, proteins and their chemical modified forms, and synthetic macromolecules, their salt forms and chemical modified forms.

4. The preparation method for biocompatible rapid-gelating hydrogel according to claim 3, wherein the polysaccharides, their salt forms and chemical modified forms include chondroitin sulfate, heparin, heparan, alginic acid, hyaluronic acid, dermatan, dermatan sulfate, pectin, carboxymethyl cellulose, chitosan, and their sodium salts or potassium salts, carboxymethylation modification, and hydrophobic modification; the proteins and their chemical modified forms include alkaline gelatin, acidic gelatin, alkaline recombinant gelatin and acidic recombinant gelatin, carboxylation modification and hydrophobic modification of an amino group; the synthetic macromolecules, their salt forms and chemical modified forms include polyacrylic acid, polyaspartic acid, polytartaric acid, polyglutamic acid, and polyfumaric acid, their sodium salts and potassium salts, carboxymethylation modification forms, and hydrophobic modification forms.

5. The preparation method for biocompatible rapid-gelating hydrogel according to claim 1, wherein the thiolation includes:
   reacting side-chain carboxylic groups of the biocompatible macromolecules with a diamine or a dihydrazide, the diamine or the dihydrazide containing disulfide bonds, to generate intermediate products, under an activation effect by a carbodiimide;
   reducing the disulfide bonds to thiols to generate the biocompatible thiolated macromolecule derivatives.

6. The preparation method for biocompatible rapid-gelating hydrogel according to claim 5, wherein the biocompatible macromolecules include hyaluronic acid, carboxymethyl hyaluronic acid, chondroitin sulphate, alkaline and acidic gelatins, alkaline and acidic recombinant gelatins, polyaspartate, and polyglutamic acid; the carbodiimides include 1-ethyl-3-(3-dimethylamine propyl) carbodiimide hydrochlorate; the diamines or the dihydrazide containing disulfide bonds include cystamine, cystine dimethylster, cystine diethylster, dithio diphenyl amine, dithio dipropyl dihydrazide, dithio dibutyl dihydrazide, dithio dipropionate diacyl glycine dihydrazide, dithio dipropionate diacyl alanine dihydrazide, dithio dipropionate diacyl (hydroxyl-) aminoacetate dihydrazide, dithio dipropionate diacyl aminopropylate dihydrazide, dithio dipropionate diacyl aminobutylate dihydrazide, dithio dibutanate diacyl glycine dihydrazide, dithio dibutanate diacyl aminopropylate dihydrazide, dimalonate diacyl cystamine dihydrazide, disuccinate diacyl cystamine dihydrazide, di(methyl) succinate diacyl cystamine dihydrazide, diglutarate diacyl cystamine dihydrazide, dihexanate diacyl cystamine dihydrazide and diheptanate diacyl cystamine dihydrazide.

7. The preparation method for biocompatible rapid-gelating hydrogel according to claim 1, wherein the thiolation includes modifying the side-chain amino group of the biocompatible macromolecule to thiol through chemical reactions.

8. The preparation method for biocompatible rapid-gelating hydrogel according to claim 1, wherein the concentration of the biocompatible thiolated macromolecule derivatives in component A is 0.5-5.0% w/v.

9. The preparation method for biocompatible rapid-gelating hydrogel according to claim 8, wherein, the concentration of the biocompatible thiolated macromolecule derivatives in component A is 0.8-3.0% w/v.

10. The preparation method for biocompatible rapid-gelating hydrogel according to claim 1, wherein the biocompatible thiol-reactive crosslinking agents are two-arm, three-arm or multi-arm polyethylene glycol derivatives containing at least two thiol-reactive functional groups, the thiol-reactive functional groups have the same or different structure,
    wherein the molecular weight of the polyethylene glycol derivatives is 100-1,000,000,
    wherein the thiol-reactive functional groups include maleimide, vinyl sulfone, $\alpha, \beta$-unsaturated acrylate, $\alpha, \beta$-unsaturated methacrylate, $\alpha, \beta$-unsaturated acrylamide, $\alpha, \beta$-unsaturated methacrylamide, iodo-propionate, bromo-propionate, chloro-propionate, iodo-propionamide, bromo-propionamide and chloro-propionamide.

11. The preparation method for biocompatible rapid-gelating hydrogel according to claim 1, wherein the component A and the component B contain a pH-buffering substance of a different concentration or a polar and hydrophilic substance.

12. The preparation method for biocompatible rapid-gelating hydrogel according to claim 1, wherein the concentration of the biocompatible thiol-reactive crosslinking agent in component B is 0.8-4.0% w/v, and the pH value range of the component B is 8.5-10.5.

13. The preparation method for biocompatible rapid-gelating hydrogel according to claim 1, wherein the chemical crosslinking reaction refers to a nucleophilic addition reaction and a nucleophilic substitution reaction between the thiol of the component A and the thiol-reactive functional group of the component B.

14. The preparation method for biocompatible rapid-gelating hydrogel according to claim 1, wherein a pH value of the reactive mixture is 8.0-12.0.

15. The preparation method for biocompatible rapid-gelating hydrogel according to claim 1, wherein a pH value range of the reactive mixture is 8.5-10.5.

16. The preparation method for biocompatible rapid-gelating hydrogel according to claim 1, wherein the reactive mixture forms the hydrogel within 1 minute of the crosslinking.

17. A preparation method for biocompatible rapid-gelating hydrogel spray, wherein the method comprises:
   filling a syringe A with a component A and filling a syringe B with a component B, wherein the component A is a solution containing biocompatible thiolated macromolecule derivatives and the component B is a solution containing biocompatible thiol-reactive crosslinking agent;
   extruding, through a four-way applicator tip, the component A from syringe A and the component B from syringe B, wherein the extruding of the component A and of the component B atomizes the component A and the component B,
   wherein a pH value of the component A is ranges from 3.5,
   wherein a pH value of the component B is more than 8.5,
   wherein the extruding mixes the component A and the component B to form a reactive mixture,
   wherein the mixing occurs under the effect of air or a gas at 1-10 atmospheric pressure,
   wherein a pH of the reactive mixture is higher than 7.0, and
   wherein the extruding sprays the reactive mixture onto a surface of an object, wherein the reactive mixture forms a hydrogel on the surface of the object.

* * * * *